US012570739B2

(12) United States Patent
Wang et al.

(10) Patent No.: US 12,570,739 B2
(45) Date of Patent: Mar. 10, 2026

(54) COMPOSITIONS AND METHODS FOR IMPROVING HEALTH THROUGH MODULATING CALHM2

(71) Applicant: PEKING UNIVERSITY, Beijing (CN)

(72) Inventors: Shiqiang Wang, Beijing (CN); Qianjin Guo, Beijing (CN); Jingruo Zhang, Beijing (CN)

(73) Assignee: PEKING UNIVERSITY, Beijing (CN)

( * ) Notice: Subject to any disclaimer, the term of this patent is extended or adjusted under 35 U.S.C. 154(b) by 1182 days.

(21) Appl. No.: 17/450,998

(22) Filed: Oct. 15, 2021

(65) Prior Publication Data

US 2022/0098298 A1     Mar. 31, 2022

Related U.S. Application Data

(63) Continuation of application No. PCT/CN2019/082674, filed on Apr. 15, 2019.

(51) Int. Cl.
| | |
|---|---|
| *C07K 16/28* | (2006.01) |
| *A61K 31/7105* | (2006.01) |
| *A61P 9/10* | (2006.01) |

(52) U.S. Cl.
CPC .......... *C07K 16/28* (2013.01); *A61K 31/7105* (2013.01); *A61P 9/10* (2018.01)

(58) Field of Classification Search
None
See application file for complete search history.

(56) References Cited

U.S. PATENT DOCUMENTS

| | | | |
|---|---|---|---|
| 8,420,309 | B2 | 4/2013 | Marambaud et al. |
| 9,725,490 | B2 | 8/2017 | Katagiri et al. |
| 2015/0259742 | A1 | 9/2015 | Zhang et al. |

OTHER PUBLICATIONS

Ma et al., "Calcium homeostasis modulator (CALHM) ion channels" 468 Pflugers Archiv—European Journal of Physiology 395-403 (Year: 2016).*

M. Djouina et al., Toxicological Consequences of Experimental Exposure to Aluminum in Human Intestinal Epithelial Cells, Food and Chemical Toxicology, 91: 108-116, 2016.

Ma, Jun et al., Calhm2 Governs Astrocytic ATP Releasing in the Development of Depression-Like Behaviors, Molecular Psychiatry, 2017, 9 pages.

Agnes Görlach et al., Calcium and ROS: A Mutual Interplay, Redox Biology, 6: 260-271, 2015.

Ashok Agarwal et al., Oxidation-Reduction Potential as a New Marker for Oxidative Stress: Correlation to Male Infertility, Investigative Clinical Urology, 58(6): 385-399, 2017.

D. Neil Granger et al., Reperfusion Injury and Reactive Oxygen Species: The Evolution of a Concept, Redox Biology, 6: 524-551, 2015.

Anna V. Kudryavtseva et al., Mitochondrial Dysfunction and Oxidative Stress in Aging and Cancer, Oncotarget, 7 (29): 44879-44905, 2016.

International Search Report in PCT/CN2019/062674 mailed on Jan. 20, 2020, 7 pages.

Written Opinion in PCT/CN2019/082674 mailed on Jan. 20, 2020, 5 pages.

* cited by examiner

*Primary Examiner* — Nancy J Leith
(74) *Attorney, Agent, or Firm* — METIS IP LLC

(57) ABSTRACT

Compositions and methods for improving health through modulating calcium homeostasis modulator 2 (CALHM2) are provided in the present disclosure. The methods may include administering, to a subject, a pharmaceutical composition including an effective amount of one or more agents that decrease CALHM2 function level in the at least one body part of the subject. The compositions may include one or more agents that decrease CALHM2 function level in at least one body part of a subject.

10 Claims, 22 Drawing Sheets

Specification includes a Sequence Listing.

FIG. 1B

Gene Code

| | |
|---|---|
| UniGene | Hs,241545 |
| RefSeq | NM_015916 |
| Symbol | FAM26B |
| Description | Homo sapiens family with sequence similarity 26, member B (FAM26B), mRNA |
| Ensembl | ENSG00000138172 |

Expressed Sequence Tag (EST) Profile (Bar chart with x-axis "Enrichment" from 0 to 4, y-axis tissues)

Uterus
Tongue
Thymus
Testis
Stomach
Spleen
Soft Tissue
Small intestine
Skin
Prostate
Placenta
PNS
Pancreas
Ovary
Muscle
Mammary gland
Lymph node
Lung
Liver
Larynx
Kidney
Heart
Eye
Colon
Cervix
Brain
Bone marrow
Bone
Blood
Bladder Enrichment

FIG. 2A

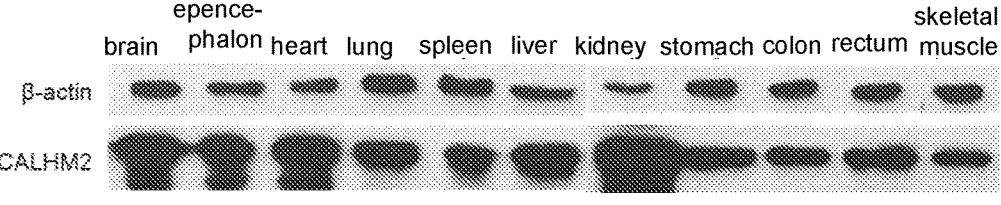

β-actin

CALHM2 brain   epence-phalon   heart   lung   spleen   liver   kidney   stomach   colon   rectum   skeletal muscle

FIG. 2B

30 min of
Ischemia 1 h of
Reperfusion

TTC staining

COMPOSITIONS AND METHODS FOR IMPROVING HEALTH THROUGH MODULATING CALHM2

CROSS-REFERENCE TO RELATED APPLICATIONS

The present disclosure is a continuation of International Application No. PCT/CN2019/082674, filed on Apr. 15, 2019, which designates the United States of America, the entire content of which is incorporated herein by reference.

SEQUENCE LISTING

The instant application contains a Sequence Listing which has been submitted electronically in TXT format and is hereby incorporated by reference in its entirety. The TXT copy, created on Oct. 15, 2021, is named "2021 Oct. 15-sequence list-20314-0002US00" and is 22,225 bytes in size.

TECHNICAL FIELD

The present disclosure generally relates to compositions and methods for improving health through modulating calcium homeostasis modulator 2 (CALHM2), and in particular, to compositions and methods for reducing reactive oxygen species (ROS) and/or ischemia-reperfusion injury by reducing the function level of CALHM2 in a subject.

BACKGROUND

CALHM2 is a member of the CALHM family of proteins and its functions were largely unknown. CALHM1, the most investigated member of this family, is known to act as a pore-forming calcium channel. However, the roles played by CALHM2, especially in the modulation of health and treatment of diseases and injuries, have not been fully explored.

ROS are chemically reactive species containing oxygen, such as peroxides, hydroxyl radical, singlet oxygen. Normal metabolic activities in various organisms may generate ROS as a by-product and ROS play an important role in cell signaling and homeostasis. However, excessive ROS and cytosolic calcium accumulation may lead to cell apoptosis. In addition, excessive ROS in mitochondria may cause damage to mitochondrial DNA, inhibit the synthesis of adenosine triphosphate (ATP), and affect the functions of the mitochondria. ROS are also linked to the aging process, as well as conditions and diseases involving inflammation. Thus, it would be beneficial and desirable to provide methods and compositions that can modulate ROS levels, thereby improving health and treat various diseases and conditions.

Various types of cells, such as but not limited to cardiomyocytes, require high levels of energy provided by mitochondria. Dysfunction in mitochondria may significantly affect the functions of some important organs, for example, the heart, the brain, the liver, etc. Ischemia-reperfusion injury is one type of injury that causes damages to at least a part of these organs. In essence, when blood supply returns to the organs or tissue after a period of ischemia, the absence and reappearance of oxygen and nutrients may result in inflammation and oxidative damage to the organs, sometimes leading to some disorders and conditions including but not limited to myocardial infarction, stroke, peripheral vascular diseases, etc. Ischemia-reperfusion injury brings much pain to patients and even threatens their lives. Therefore, it is beneficial and desirable to develop compositions and methods for the reduction of ischemia-reperfusion injury.

SUMMARY

According to an aspect of the present disclosure, a method of reducing reactive oxygen species (ROS) in at least one body part of a subject suffering from an ROS-related disease or condition is provided. The method may include administering, to the subject, a pharmaceutical composition including an effective amount of one or more agents that decrease calcium homeostasis modulator 2 (CALHM2) function level in the at least one body part of the subject.

In some embodiments, the subject may be a human or animal.

In some embodiments, the ROS-related disease or condition may be aging, infertility or cancer.

In some embodiments, the subject may be a human and the ROS-related disease or condition may be aging.

In some embodiments, the subject may be a human male and the ROS-related disease or condition may be male infertility.

In some embodiments, the subject may be a human and the ROS-related disease or condition may be cancer.

In some embodiments, the at least one body part of the subject may include the uterus, spleen, or heart of the subject.

In some embodiments, the at least one body part of the subject may include the heart of the subject.

In some embodiments, the one or more agents may be configured to decrease CALHM2 function level to reduce basal ROS in the heart of the subject.

In some embodiments, the one or more agents may be configured to decrease CALHM2 function level to reduce basal ROS in the cardiomyocyte mitochondria of the subject.

In some embodiments, the one or more agents may be configured to decrease CALHM2 function level to reduce basal ROS by at least 20% in the cardiomyocyte mitochondria of the subject.

According to another aspect of the present disclosure, a method of reducing ischemia-reperfusion injury in a subject is provided. The method may include administering, to the subject, a pharmaceutical composition including one or more agents that decrease calcium homeostasis modulator 2 (CALHM2) function level in at least one body part of the subject's circulatory system.

In some embodiments, the subject may be a human or animal.

In some embodiments, the subject may be suffering from cardiac ischemia.

In some embodiments, the subject may be suffering from bowel ischemia, brain ischemia, limb ischemia, or cutaneous ischemia.

In some embodiments, the at least one body part of the subject may include the heart of the subject.

In some embodiments, the pharmaceutical composition may be administered to the subject before a reperfusion occurs in the body part of the subject.

In some embodiments, the pharmaceutical composition may be administered to the subject after a reperfusion occurs in the body part of the subject.

In some embodiments, the pharmaceutical composition may be administered to the subject after the subject has suffered from ischemia.

In some embodiments, the pharmaceutical composition may be administered to the subject before the subject suffers from ischemia.

In some embodiments, the one or more agents may be configured to decrease CALHM2 function level by reducing CALHM2 protein expression in the at least one body part.

In some embodiments, the one or more agents may be configured to reduce CALHM2 protein expression by reducing CALHM2 cDNA level in the at least one body part.

In some embodiments, the one or more agents may be configured to reduce CALHM2 protein expression by reducing CALHM2 mRNA level in the at least one body part.

In some embodiments, the one or more agents may be part of a CRISPR-Cas9 system.

In some embodiments, the one or more agents may include siRNAs that down-regulate CALHM2 expression.

In some embodiments, the one or more agents may include aptamers that down-regulate CALHM2 expression.

In some embodiments, the one or more agents may include a CALHM2 antibody.

In some embodiments, the one or more agents may be configured to decrease CALHM2 function level by reducing CALHM2 protein function as part of a membrane channel in cells of the at least one body part.

In some embodiments, the one or more agents may include an antagonist of CALHM2.

In some embodiments, the one or more agents may include a blocker of the transmembrane channel.

In some embodiments, the one or more agents may include an engineered carrier vector comprising a DNA sequence that may be configured to induce CALHM2 degradation.

In some embodiments, the one or more agents may include an engineered virus comprising a DNA sequence that may be configured to induce CALHM2 degradation.

In some embodiments, the virus may include adenosine associated virus, adenosine virus, lentivirus, or sendai virus.

In some embodiments, the one or more agents may be configured to decrease CALHM2 expression by stimulating a negative factor that enhances CALHM2 expression.

In some embodiments, the one or more agents may be configured to decrease CALHM2 expression by inhibiting a positive factor that increases CALHM2 expression.

In some embodiments, the one or more agents may be configured to decrease CALHM2 activity by stimulating a negative factor that reduces CALHM2 activity.

In some embodiments, the one or more agents may be configured to decrease CALHM2 activity by inhibiting a positive factor that increases CALHM2 activity.

In some embodiments, administering to the subject the pharmaceutical composition may include administering the pharmaceutical composition to the skin of the subject.

In some embodiments, administering to the subject the pharmaceutical composition may comprise injecting the pharmaceutical composition to the subject.

In some embodiments, administering to the subject the pharmaceutical composition may include administering orally the composition to the subject.

In some embodiments, the composition may be configured as a suppository.

According to still another aspect of the present disclosure, a method for slowing the progression of, or preventing aging, infertility or cancer in a human suffering aging, infertility or cancer is provided. The method may include administering, to the subject, a pharmaceutical composition including an effective amount of one or more agents that decrease calcium homeostasis modulator 2 (CALHM2) function level in the at least one body part of the human.

According to yet another aspect of the present disclosure, a method of reducing ischemia-reperfusion injury in a human or animal suffering from ischemia. The method may include administering, to the human or animal, a pharmaceutical composition including one or more agents that decrease calcium homeostasis modulator 2 (CALHM2) function level in at least one body part of the subject's circulatory system, before a reperfusion occurs in the body part of the human or animal.

In some embodiments, the one or more agents may be configured to decrease CALHM2 function level to inhibit mitochondrial permeability transition pore (mPTP) function.

In some embodiments, the one or more agents may be configured to decrease CALHM2 function level to inhibit mPTP responsiveness to $Ca^{2+}$ stimuli at low concentration.

In some embodiments, the one or more agents may be configured to decrease CALHM2 function level to reduce cristae junction distance in cardiomyocytes of the subject.

In some embodiments, the one or more agents may be configured to decrease CALHM2 function level to reduce cardiomyocyte resistance to $Ca^{2+}$ influx.

In some embodiments, the one or more agents may be configured to decrease CALHM2 function level to reduce oxygen consumption in cardiomyocytes of the subject.

According to still another aspect of the present disclosure, a composition configured to treat, slow the progression of, or prevent aging, infertility or cancer, or reduce ischemia-reperfusion injury, in a subject is provided. The composition may include one or more agents that decreases CALHM2 function level in at least one body part of the subject.

In some embodiments, the subject may be a human or animal.

In some embodiments, the at least one body part of the subject may include the heart of the subject.

In some embodiments, the one or more agents may be configured to decrease CALHM2 protein expression in the at least one body part.

In some embodiments, the one or more agents may be configured to reduce CALHM2 cDNA in the at least one body part.

In some embodiments, the one or more agents may be configured to decrease CALHM2 activity in the at least one body part.

In some embodiments, the one or more agents may be configured to block a transmembrane channel that may include CALHM2.

In some embodiments, the one or more agents may include an antibody or an siRNA.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. It should be noted that the drawings are not to scale. These embodiments are non-limiting exemplary embodiments, in which like reference numerals represent similar structures throughout the several views of the drawings, and wherein:

FIG. 1B is an analytical graph of an exemplary comparison of the amino acid sequences of the CALHM2 proteins of some species, as used in some embodiments of the present disclosure;

FIG. 2A is an analytical graph illustrating an exemplary expression of CALHM2 in various organs and tissues according to some embodiments of the present disclosure;

FIG. 2B is a graph illustrating results of an exemplary western blot analysis for evaluating the expression of CALHM2 in various organs and tissues of mice according to some embodiments of the present disclosure;

DETAILED DESCRIPTION

Figure 1A:
FIG. 1A is an exemplary cladogram showing CALHM2 lineage.

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but is to be accorded the widest scope consistent with the claims.

The terminology used herein is to describe particular example embodiments only and is not intended to be limiting. As used herein, the singular forms "a," "an," and "the" may be intended to include the plural forms as well, unless the context clearly indicates otherwise. It will be further understood that the terms "comprises," "comprising," "includes," and/or "including" when used in this specification, specify the presence of stated features, integers, steps, operations, elements, and/or components, but do not preclude the presence or addition of one or more other features, integers, steps, operations, elements, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawing(s), all of which form a part of this specification. It is to be expressly understood, however, that the drawing(s) are for the purpose of illustration and description only and are not intended to limit the scope of the present disclosure. It is understood that the drawings are not to scale.

According to some embodiments of the present disclosure, compositions and methods of improving health of a subject (human or animal) are provided. In some embodiments, the improvement of health is achieved by treating a disease or condition (e.g., an injury). In some embodiments, the improvement of health is achieved by slowing, reducing, or stopping a detrimental process (e.g., aging). In some embodiments, the improvement of health is achieved by modulating (increasing or decreasing) CALHM2 function level. In some embodiments, the improvement of health is achieved by modulating CALHM2 function level with a composition that includes one or more agents that effectively increase or decrease CALHM2 function level.

As used herein, the term "function level" of the CALHM2 protein refers to a capability of performing normal functions of the CALHM2 in a subject or at least one body part of the subject. The function level of the CALHM2 protein may be affected by CALHM2 protein expression (or local concentration of CALHM2 protein), which may be changed through the modulation of CALHM2 DNA or mRNA levels, or through a direct modulation of CALHM2 protein expression (e.g., translation of mRNA to protein) without changing nucleic acid levels. The function level of the CALHM2 protein may also be affected by modulating CALHM2 activity (functioning level of CALHM2 per unit CALHM2 protein) with modulators, such as but not limited to antibodies, antagonists, and agonists of CALHM2 function, without affecting protein expression.

In some embodiments, the improvement of health is achieved by modulating (increasing or decreasing) CALHM2 protein expression. In some embodiments, the improvement of health is achieved by modulating (increasing or decreasing) CALHM2 activity. In some embodiments, the improvement of health is achieved by modulating (increasing or decreasing) both CALHM2 protein expression and CALHM2 activity. In certain embodiments, the one or more agents are configured to modulate (increase or decrease) CALHM2 protein expression. In certain embodiments, the one or more agents are configured to modulate (increase or decrease) CALHM2 activity. In certain embodiments, the one or more agents are configured to modulate (increase or decrease) both CALHM2 protein expression and CALHM2 activity.

In some embodiments of the present disclosure, methods and composition for reducing ROS in at least one body part of a subject are provided. In some embodiments, the composition may include an effective amount of one or more agents that decrease calcium homeostasis modulator 2 (CALHM2) function level in the at least one body part of the subject. In some embodiments, the method may include administering, to the subject, a composition including an effective amount of one or more agents that decrease CALHM2 function level in the at least one body part of the subject.

In some embodiments, the subject may be a human or an animal. For example, the subject may be a human. In some embodiments, the subject may be an infant, a child, a teenager, a middle-aged adult, or a senior adult. In some embodiments, the subject may be a male human. In some embodiments, the subject may be a female human. Exemplary animals may include a bovine, a sheep, a pig, an elephant, a panda, a dog, a cat, a monkey a chimpanzee, a macaque, a rabbit, a rat, a mouse, a zebrafish, a sea turtle, or the like. In some embodiments, the subject may be a mammal. In some embodiments, the subject may include a companion animal (also referred to as a "pet"), an animal of a protected species, an animal for scientific research, an animal assisting police services (e.g., a police dog), or the like, or any combination thereof.

In some embodiments, the subject may be suffering from an ROS-associated disease or condition. In some cases, ROS are a by-product generated during metabolic activities (e.g., cell respiration). For example, excessive accumulation of ROS and calcium (e.g., in the form of $Ca^{2+}$) may cause the opening of mitochondrial permeability transition pore (mPTP) and the decrease of inner mitochondrial membrane potential. This may result in swelling and subsequent rupture of mitochondria. Additionally or alternatively, pro-death signals (e.g., cytochrome c) may be released, which may lead to cell apoptosis. Excessive ROS may cause DNA damage, enhance proliferation of cancer cells, inhibit the synthesis of adenosine triphosphate (ATP), or the like. Thus, excessive ROS may affect the functions of mitochondria and the functions of certain cells. In some embodiments, the excessive ROS may be associated with one or more diseases. For instance, cardiomyocytes need much energy (provided by ATP) for cardiac excitation-contraction coupling. Dysfunctions of the mitochondria may cause a disease or disorder of the heart. The one or more diseases may include but not limited to a cardiovascular disease, an Alzheimer's disease, a neurodegeneration disease, cancer, diabetes, infertility (e.g., male infertility), or the like, or any combination thereof. In some embodiments, ROS may be associated with aging. In some embodiments, the subject may not be suffering from any ROS-associated disease or condition.

In some embodiments, the composition for reducing the ROS provided in the present disclosure may include an effective amount of one or more agents that decrease the CALHM2 functional level. The CALHM2 protein is a protein from the CALHM family and is present in various species (as will be described in Example 1), such as human, mouse, pig, dog, frog, sea turtle, zebrafish, etc, in varying but highly similar forms. See FIG. 1A, which shows an evolutionary lineage of CALHM2.

The CALHM2 protein is expressed in various organs and tissues. For example, the CALHM2 protein is abundant in the brain, the heart, the kidney, the liver, the uterus, etc. In addition, the CALHM2 protein is mainly expressed in the mitochondria, as evidenced by co-localization studies showing CALHM2 protein expression and mitochondria markers.

In some embodiments, the CALHM2 protein may serve as part of a membrane channel in cells of the at least one body part. In some embodiments, CALHM2 protein may affect the morphology of mitochondria. For example, the decrease of the CALHM2 functional level may increase a density of distribution of cristae in the mitochondria (or reduce the cristae junction distance for the mitochondria, as will be described in Example 4 and Example 7). In some embodiments, the decrease of the CALHM2 functional level may affect the metabolism of mitochondria. For example, the decrease of the CALHM2 function level may lead to reduced maximum oxygen consumption rate (OCR) of the mitochondria (as will be described in Example 5). In some embodiments, the decrease of the CALHM2 functional level may result in a lower level of basal ROS (as will be described in Example 8). In some embodiments, the decrease of the CALHM2 functional level may have strong effects on the metabolic activities of cardiomyocytes, such as the respiration (as described in Example 8). In some embodiments, the decrease of the CALHM2 functional level may inhibit mPTP function. Specifically, the decrease of the CALHM2 function level may inhibit mPTP responsiveness (e.g., opening of the mPTP) to $Ca^{2+}$ stimuli at low concentration. In some embodiments, the decrease of the CALHM2 functional level may reduce cardiomyocyte resistance to $Ca^{2+}$ influx. In some embodiments, the decrease of the CALHM2 functional level may reduce oxygen consumption in cardiomyocytes of the subject.

In some embodiments, the one or more agents in the composition may decrease the CALHM2 functional level to reduce basal ROS in the at least one body part of the subject, such as the brain, the heart, the kidney, the uterus, various tissue, or cells, or the like. In some embodiments, the one or more agents may be configured to decrease the CALHM2 functional level to reduce basal ROS in the cardiomyocytes (e.g., in the cardiomyocyte mitochondria) of the subject. In some embodiments, the one or more agents may be configured to decrease the CALHM2 functional level by at least 5%, 10%, 20%, 30%, 40%, 50%, 60%, 70%, 80%, 90%, or 95%. In some embodiments, the one or more agents may be configured to decrease the CALHM2 functional level by at least 30%, 40%, 50%, 60%, 70%, 80%, or 90%. In some embodiments, the one or more agents may be configured to decrease the CALHM2 functional level by at least 50%, 60%, or 70%. In some embodiments, the one or more agents may be configured to decrease the CALHM2 functional level by around 60%.

In some embodiments, the one or more agents may be configured to decrease the CALHM2 protein expression by at least 5%, 10%, 20%, 30%, 40%, 50%, 60%, 70%, 80%, 90%, or 95%. In some embodiments, the one or more agents may be configured to decrease the CALHM2 protein expression by at least 30%, 40%, 50%, 60%, 70%, or 80%. In some embodiments, the one or more agents may be configured to decrease the CALHM2 protein expression by at least 50%, 60%, or 70%. In some embodiments, the one or more agents may be configured to decrease the CALHM2 protein expression by around 60%. In some embodiments, the one or more agents may be configured to decrease the CALHM2 protein activity by at least 5%, 10%, 20%, 30%, 40%, 50%, 60%, 70%, 80%, 90%, or 95%. In some embodiments, the one or more agents may be configured to decrease the CALHM2 protein activity by at least 30%, 40%, 50%, 60%, 70%, 80%.

In some embodiments, the one or more agents may be configured to decrease the CALHM2 functional level to reduce basal ROS in the at least one body part of the subject by at least 5%, 10%, 15%, 20%, 30%, 40%, 50%, 60%, 70%, 80%, 90%, or 95%. In some embodiments, the one or more agents may be configured to decrease the CALHM2 functional level to reduce basal ROS in the at least one body part of the subject by at least 15%, 20%, 30%, 40%, 50%, 60%, or 70%. In some embodiments, the one or more agents may be configured to decrease the CALHM2 functional level to reduce basal ROS in the at least one body part of the subject by at least 30%, 40%, or 50%. In some embodiments, the one or more agents are configured to reduce basal ROS in the at least one body part of the subject by decreasing CALHM2 protein expression. In some embodiments, the one or more agents are configured to reduce basal ROS in the at least one body part of the subject by decreasing CALHM2 protein activity. In some embodiments, the one or more agents are configured to reduce basal ROS in the at least one body part of the subject by decreasing both CALHM2 protein expression and CALHM2 protein activity.

In some embodiments, a method of using the composition may include administering the composition to the subject to prevent, slow, or stop the progression of, or treat the one or more ROS-associated diseases or conditions. For instance, the composition may be configured to reduce or eliminate one or more symptoms of the one or more ROS-associated diseases, such as the cardiovascular disease, the Alzheimer's disease, the neurodegeneration disease, the cancer, the diabetes, the infertility (e.g., male infertility), or the like, or any combination thereof. Specifically, the cardiovascular disease may include but not limited to angina, myocardial infarction, stroke, heart failure, hypertensive heart disease, rheumatic heart disease, cardiomyopathy, heart arrhythmia, congenital heart disease, carditis, peripheral artery disease, thromboembolic disease, venous thrombosis, or the like, or any combination thereof. The cancer may include but not limited to non-small cell lung cancer (NSCLC), rhabdomyosarcoma, breast cancer, bladder cancer, colorectal cancer, kidney cancer, leukemia, liver cancer, lung cancer, lymphoma, pancreatic cancer, prostate cancer, skin cancer, thyroid cancer, melanoma, oral and oropharyngeal cancer, uterine cancer, or the like, or any combination thereof. As another example, the composition may be configured to prevent the cancer and/or slow an aging process. Specifically, the composition may be configured to slow the aging process of the at least one body part of the subject, such as the brain, the heart, the lung, the kidney, the skin, etc.

According to another aspect of the present disclosure, a composition of reducing ischemia-reperfusion injury in at least one body part of a subject's circulatory system is provided. In some embodiments, the composition may include an effective amount of one or more agents that decrease CALHM2 function level in the at least one body part of the subject. A method of using such composition is also provided.

In some embodiments, the subject may be suffering from ischemia in the at least one body part. The ischemia may cause a shortage of oxygen and/or nutrients need for cellular metabolism, thus leading to damage or dysfunctions of the at least one body part. In some embodiments, reperfusion after a certain period of ischemia may not be able to restore the normal functions of at least a portion (e.g., cells, tissue, or an organ) of the at least one body part. Such injury is referred to as the ischemia-reperfusion injury. Merely by way of example, the ischemia may be caused by the presence of blood clots, inflammation of blood vessels, plaque buildup in arteries, narrowing or blockage of blood vessels, trauma, etc. In some embodiments, the subject may be suffering from cardiac ischemia, bowel ischemia, brain ischemia, kidney ischemia, spleen ischemia, limb ischemia, cutaneous ischemia, or the like, or any combination thereof. Alternatively, the subject may not be suffering from any ischemia.

In some embodiments, the composition for reducing the ischemia-reperfusion injury may include an effective amount of one or more agents that decrease the CALHM2 functional level. In some embodiments, the decrease of CALHM2 functional level may decrease the infarct size of the at least one body part (e.g., the heart) after ischemia, as will be described in Example 9. In some embodiments, the decrease of the CALHM2 functional level may have a specific effect on the metabolic activities of cardiomyocytes, such as the respiration (as described in Example 8). In some embodiments, the decrease of the CALHM2 functional level may reduce cardiomyocyte resistance to $Ca^{2+}$ influx. In some embodiments, the decrease of the CALHM2 functional level may reduce oxygen consumption in cardiomyocytes of the subject.

In some embodiments, a method of using the composition may include administering the composition to the subject to prevent, slow the progression of, or treat the one or more diseases or conditions associated with the ischemia-reperfusion injury. The one or more diseases or conditions may include anemia, a coronary artery disease, a peripheral artery occlusive disease, stroke, heart failure, localized necrosis, or the like, or any combination thereof. In some embodiments, the composition may be configured to prevent or reduce the ischemia-reperfusion injury of the cardiomyocytes. In some embodiments, the composition may be administered to the subject before the subject suffers from ischemia in the at least one body part of the subject to prevent or reduce a possible ischemia-reperfusion injury. Additionally or alternatively, the composition may be administered to the subject after the subject has suffered from ischemia in the at least one body part of the subject to reduce the ischemia-reperfusion injury. In some embodiments, the composition may be administered to the subject before a reperfusion occurs in the at least one body part of the subject. In some embodiments, the composition may be administered to the subject after a reperfusion occurs in the at least one body part of the subject.

In some embodiments, the one or more agents for the composition that reduces ROS or the ischemia-reperfusion injury in the at least one body part may decrease the CALHM2 functional level by decreasing the amount of CALHM2 protein in the at least one body part, and/or reduce CALHM2 protein activity. As used herein, the CALHM2 protein refers to a full length of CALHM2 protein, or a fragment of the CALHM2 protein that retains the function of the CALHM2 protein.

In some embodiments, the one or more agents may be configured to reduce CALHM2 protein expression, for example, by reducing CALHM2 cDNA level in the at least one body part. In some embodiments, the one or more agents may be configured to knock out or knock down the DNA sequence encoding the CALHM2 protein. In some embodiments, the one or more agents may be part of a clustered regularly interspaced short palindromic repeats-Cas9 (CRISPR-Cas9) system. For example, the one or more agents may include a guide RNA (gRNA) complexed with a Cas9 protein. The gRNA may match with the DNA sequence encoding the CALHM2 protein. The coupled Cas9 may cause a double stranded break in the DNA sequence encoding the CALHM2 protein and may result in a frameshift mutation that silences the DNA sequence encoding the CALHM2 protein. In some embodiments, the one or more agents may include a CRISPR-Cas9 vector for expressing the Cas9 protein and the gRNA in a cell.

In some embodiments, the one or more agents may be configured to reduce CALHM2 mRNA level in the at least one body part. For example, the one or more agents may include a microRNA (miRNA), an antisense DNA, a small interfering RNA (siRNA), an aptamer, or the like, or any combination thereof. In some embodiments, the miRNA, the antisense DNA and/or a complementary strand of the siRNA may bind to a CALHM2 mRNA sequence or a fragment of the CALHM2 mRNA sequence via a base-paring mechanism, so that the CALHM2 mRNA sequence may be silenced, and accordingly, the expression of CALHM2 peptide may be inhibited.

In some embodiments, the one or more agents configured to decrease the amount of the CALHM2 protein may induce the degradation of CALHM2 protein or the DNA sequence encoding the CALHM2 protein. In some embodiments, the one or more agents may include an engineered carrier vector including a DNA sequence that induces the degradation of CALHM2 protein or the DNA sequence encoding the CALHM2 protein. Merely by way of example, the engineered carrier vector may include a bacterial plasmid, a cosmid, a viruses, etc. For instance, the viruses may include a bacteriophage, an adenosine virus, an adenosine associated virus, a sendai virus (SeV), a retrovirus, a polyomavirus, an Epstein-Barr virus, or the like, or any combination thereof. In some embodiments, the retrovirus may include one or more viruses from an Alpharetrovirus genus (e.g., an Avian leucosis virus), a Beltaretrovirus genus (e.g., a mouse mammary tumor virus), a Gammaretrovirus genus (e.g., a Murine leukemia virus), a Deltaretrovirus genus (e.g., a bovine leukemia virus), an Epsilonretrovirus genus (e.g., a Walleye dermal sarcoma virus), a Lentivirus genus (e.g., a human immunodeficiency virus), a Spumavirus genus (e.g., a simian foamy virus), or the like, or any combination thereof.

In some embodiments, the one or more agents may be configured to decrease CALHM2 expression by stimulating a negative factor that enhances CALHM2 expression. In some embodiments, the one or more agents may be configured to decrease CALHM2 expression by inhibiting a positive factor that increases CALHM2 expression.

In some embodiments, the one or more agents for reducing the CALHM2 protein activity may include a CALHM2 antibody. The CALHM2 antibody may bind with the CALHM2 protein and affect the interactions of the CALHM2 protein with other proteins or factors, and thus may reduce the CALHM2 protein function. Merely by way of example, the antibody may include IgG, IgM, IgA, IgD or IgE molecules, or an antigen-specific fragment thereof (e.g., a Fab fragment, a Fv fragment, a scFv fragment, a single domain antibody, a disulphide-linked scfv fragment, or the like).

In some embodiments, the one or more agents may be configured to inhibit the function of the CALHM2 proteins, for example, as part of a membrane channel in cells of the at least one body part, or as a modulator for metabolic activities of the mitochondria, or the like. The one or more agents may include an antagonist of CALHM2. In some embodiments, the one or more agents may include a blocker of the transmembrane channel (e.g., a $Ca^{2+}$ channel) of the cells in the at least one body part. Merely by way of example, the blocker of the $Ca^{2+}$ channel may include dihydropyridine, phenylalkylamine, benzothiazepine, mibefradil, bepridil, flunarizine, fluspirilene, fendiline, gabapentin, pregabalin, ziconotide, or the like, or any derivative thereof, or any combination thereof.

In some embodiments, the composition for reducing the ROS and/or the ischemia-reperfusion injury in the at least one body part may be orally administered to the subject. In some embodiments, the composition may be a pharmaceutical formulation used as a drug. In some embodiments, the composition for oral administration may be formulated as a dietary supplement, a food additive, a drink additive, or the like, or any combination thereof. In some embodiments, the composition may be formulated in the form of tablets, granules, powder, micellas, liquids, suspensions, emulsions, or the like, or any combination thereof. In some embodiments, the composition may include a pharmaceutically acceptable carrier. The pharmaceutically acceptable carrier may be nontoxic and may not have a negative impact on the activity of the agent(s) that decreases the CALHM2 function level in the composition. For instance, the pharmaceutically acceptable carrier may include an excipient, a diluent, an auxiliary component, or the like, or any combination thereof. Exemplary excipients may include but are not limited to an emulsifier, a flow agent, a flavoring agent, a coloring agent, or the like, or any combination thereof. In some embodiments, the pharmaceutically acceptable carrier may protect the agent(s) against oxidation and/or degradation caused by enzymes and low/high pH values, so as to maintain the efficacy of the composition. For instance, the pharmaceutically acceptable carrier may include a coating layer, a capsule, a microcapsule, a nanocapsule, or the like, or any combination thereof. In some embodiments, the pharmaceutically acceptable carrier may have a capability of a controlled release of the agent(s) that decreases the CALHM2 function level. The controlled release may include but is not limited to a slow release, a sustained release, a targeted release, or the like, or any combination thereof. Merely by way of example, the pharmaceutically acceptable carrier may include hydrogel capsules, microcapsules or nanocapsules made of collagen, gelatin, chitosan, alginate, polyvinyl alcohol, polylactic acid, or the like, or any combination thereof.

In some embodiments, the composition for reducing the ROS and/or the ischemia-reperfusion injury in the at least one body part may be a parenteral formulation. For example, the composition may be an injection formulation as a solution, a suspension, an emulsion, powder, or the like. In some embodiments, the composition in the form of powder may be dissolved or dispersed in a solution, a suspension or an emulsion before injection. In some embodiments, the injection formulation may further include other pharmaceutically injectable ingredients, such as glucose, sodium chloride, potassium chloride, or the like, or any combination thereof. In some embodiments, the composition may be administered to the subject via intravenous injection or intraperitoneal injection. In some embodiments, the composition may be stereotactically injected into the at least one body part or a region near the at least one body part to decrease the CALHM2 function level in the at least one body part. For example, the composition may be administered to or near the heart, the kidney, the liver, the spleen, or the like, or any combination thereof. In some embodiments, the composition may be formulated as (or configured as) a suppository. As used herein, a "suppository" refers to a dosage form that is put in the rectum, vagina, urethra, or the like, or any combination thereof. In some embodiments, the suppository may include a pharmaceutically acceptable carrier that contains the active ingredients of the composition (e.g., the one or more agents that decrease the CALHM2 function level). In some embodiments, the pharmaceutically acceptable carrier may gradually dissolve, melt, or degrade (e.g., in the rectum, vagina, urethra) to release the active ingredients for local or systemic effects. In some embodiments, the composition may be administered to the subject via vaginal administration, rectal administration, nasal administration (e.g., in the form of a nose drop), auricular administration (e.g., in the form of an ear drop), intramedullary administration, intra-articular administration, intrapleural administration, or the like, or any combination thereof. In some embodiments, the composition may be applied to the skin of the subject. For instance, the composition may be formulated as powder, granules, nanoparticles, cream, a lotion, an ointment, a suspension, a solution, or the like. Merely by way of example, the composition may be smeared or sprayed onto the skin of the subject (e.g., the skin of the at least one body part, the skin near the at least one body part).

In some embodiments, the composition may be administered to the subject once a day, twice a day, three times a day, four time a day, etc. In some embodiments, the composition may be administered to the subject once every other day, once every three days, once a week, once every two weeks, once a month, etc.

The present disclosure is further described according to the following examples, which should not be construed as limiting the scope of the present disclosure.

EXAMPLES

Materials and Methods

Animals

The rats used in the Examples were male rats from the Sprague-Dawley (SD) strain. The mice used in the Examples were mice from the C57BL/6 strain.

CALHM2 knocked-out (KO) mice were obtained by using a homologous recombination technique to knock out CALHM2 in C57BL/6 mice. Exons 2-3 of the CALHM2 cDNA were replaced by loxp-neo-loxp in C57BL/6 mice, and then the C57BL/6 mice were crossed with mice having the Cre recombinase to remove the neo resistance gene. A genotype identification test was carried out to distinguish wild type (WT) mice and the KO mice. Genome DNA of the resultant mice was extracted from their tails for a Polymerase Chain Reaction (PCR) test. The PCR test was conducted using the following primers: CALHM2-gtWTF (sequence shown in SEQ ID NO: 1), CALHM2-gtR1 (sequence shown in SEQ ID NO: 2), and Zmk2F4 (sequence shown in SEQ ID NO: 3).

Isolation of Cardiomyocytes.

Cardiomyocytes were isolated from adult male mice of two to four months old. Specifically, heparin sodium was injected to a mouse for anticoagulation. The mouse was anesthetized, and the heart of the mouse was removed. The heart was subjected to a first perfusion process using ethylene glycol-bis(β-aminoethyl ether)-N, N,N', N'-tetraacetic acid (EGTA) tyrode solution, and a second perfusion process using an enzyme solution. Then the ventricular tissue was minced into small pieces and dispersed in another enzyme solution to obtain a suspension liquid. The suspension liquid was centrifuged to obtain cell sediments. The cell sediments were re-suspended in a cell preservation liquid.

Liposome Transfection

Frozen COS-7 cells were resuscitated and subjected to a cell passage process. The CALHM2 gene in COS-7 cells were knocked down using a CRISPR-Cas9 system. Small guided RNAs (sgRNAs) used in the CRISPR-Cas9 system were produced based on the CALHM2 gene coding sequence. The primer sequence for coding the sgRNAs is shown in SEQ ID NO. 4 (Forward, CACCGTCCGGCCCCGAGGAGGCC) and SEQ ID NO. 5 (Reverse, AAACTGGCCTCCTCGGGGCCGGAC). The COS-7 cells were cultured and added into opti-MEM culture medium. The plasmid and the transfection reagent lipo 2000 were added into 500 μL opti-MEM culture medium, respectively, and incubated under room temperature for 5 min. The opti-MEM culture media including the plasmid and the transfection reagent lipo 2000 were mixed and incubated under room temperature for 15 to 20 min, and then the mixture was added into the opti-MEM culture medium including the COS-7 cells and incubated for 6 h. The opti-MEM culture medium was replaced by DMEM+10% FBS culture medium. The cells were cultured under 37° C. and 5% carbon dioxide for 48 h. A flow cell sorter was used to distinguish COS-7 cells transfected with the plasmid used for knocking down CALHM2, so as to obtain knocked-down (KD) cells. The COS-7 cells were treated with the same transfection reagents but without the plasmid used for knocking down CALHM2, so as to obtain MOCK cells. The MOCK cells were used as a control group for evaluating various effects of knocking down CALHM2 in COS-7 cells.

Measurement of the Level of CALHM2 Expression

The levels of expression of CALHM1, CALHM2, and CALHM3, in the hearts of the wild type mice were measured, respectively. The mRNA of CALHM1, CALHM2, and CALHM3 was extracted from minced heart tissue of the wild type mice using solvents. The extracted mRNA was rinsed and dried, respectively. The mRNA was used for reverse transcription. A solution including oligodT, dNTP, ddH$_2$O and 2 μg of the mRNA were heated to 65° C. for 5 min and cooled using ice. 5× RT PCR buffer, dithiothreitol, RNASEOUT™ recombinant ribonuclease inhibitor, and SUPERSCRIPT™ III Rtase were added in the solution. The solution was kept under 25° C. for 5 min, and then heated to 50° C. and maintained at 50° C. for 60 min for extension. The solution was further heated to 70° C. and maintained at 70° C. for 15 min for reverse transcription to obtain cDNA. The cDNA was diluted and used as a template for a fluorescent quantative PCR. The primers for the fluorescent quantative PCR were designed using the Primer Premier 5 software. A reaction mixture was prepared, using 1 μL of the cDNA template, 5 μL of 2×QPCR SuperMix, 1 μL of forward primer, 1 μL of reverse primer, and 2 μL of ddH$_2$O.

The PCR was performed using the reaction mixture. The MxPro software was used for a quantative analysis on the PCR results with reference to GAPDH gene. The primers used are listed in the following Table 1.

TABLE 1

| primers used in the measurement of the level of expression of CALHM2 | | | |
| --- | --- | --- | --- |
| Gene | Species | Forward primer | Reverse Primer |
| CALHM2 | mouse | SEQ ID NO: 6 | SEQ ID NO: 7 |
| CALHM2 | rat | SEQ ID NO: 8 | SEQ ID NO: 9 |
| CALHM1 | rat | SEQ ID NO: 10 | SEQ ID NO: 11 |
| CALHM3 | rat | SEQ ID NO: 12 | SEQ ID NO: 13 |
| GAPDH | mouse/rat | SEQ ID NO: 14 | SEQ ID NO: 15 |

Measurement of Functions of Mitochondria

The mitochondria were isolated using a mitochondria isolation kit (Beyotime, C3606). To perform a mitochondrial swelling assay, 10 μL of a solution containing mitochondria was added to 200 μL of swelling buffer. CaCl$_2$) solution was added to the mixture to stimulate the mitochondria. The absorbance at 540 nm of the resultant mixture changed with time and was monitored using a spectrophotometer. The isolated mitochondria were also used for measuring the membrane potential using a membrane potential testing kit (Beyotime, 2006). JC-1 was used to stain the mitochondria. Changes of the membrane potential were monitored by measuring the fluorescence of the JC-1.

Metabolic Analysis

A Seahorse analyzer (Seahorse, Bioscience, XFe24) was used to measure the oxygen consumption rate (OCR) of the mitochondria. Oligomycin, carbonyl cyanide-4-trifluoromethoxyphenylhydrazone (FCCP), and antimycin was added during the measurement. Basal respiration rate was obtained by subtracting non-mitochondria respiration rate from the OCR before adding oligomycin. Basal respiration rate was normalized based on the concentration of the proteins in the mixture.

Ischemia-Reperfusion Test

The heart removed from the WT mice and the KO mice (at the age of about 8 weeks, and body weight between 23 to 25 g) were hung on a langendorf device to perform a reverse perfusion process using a Krebs Henseleit (K-H) solution. The perfusion lasted for 30 min to remove remaining blood in the heart. The perfusion was stopped to induce ischemia. 12A is a schematic diagram illustrating results of an exemplary ischemia-reperfusion test according to some embodiments of the present disclosure. After 30 min of ischemia, the K-H solution was used to re-perfuse the heart. Then the heart was removed from the langendorf device and stained using 1% 2,3,5-triphenyl tetrazolium chloride (TTC) solution, so as to distinguish infract area and normal area.

Example 1 the Conservativeness of CALHM2 Protein

The conservativeness of CALHM2 proteins in their amino acid sequences among various species was evaluated using bioinformatics techniques. FIG. 1A is an exemplary cladogram showing CALHM2 lineage. The cladogram was obtained using the MEGA software. As shown in FIG. 1A, CALHM2 is present in various species, such as but not limited rat, zebrafish, human, frog, etc.

Figure 1B:
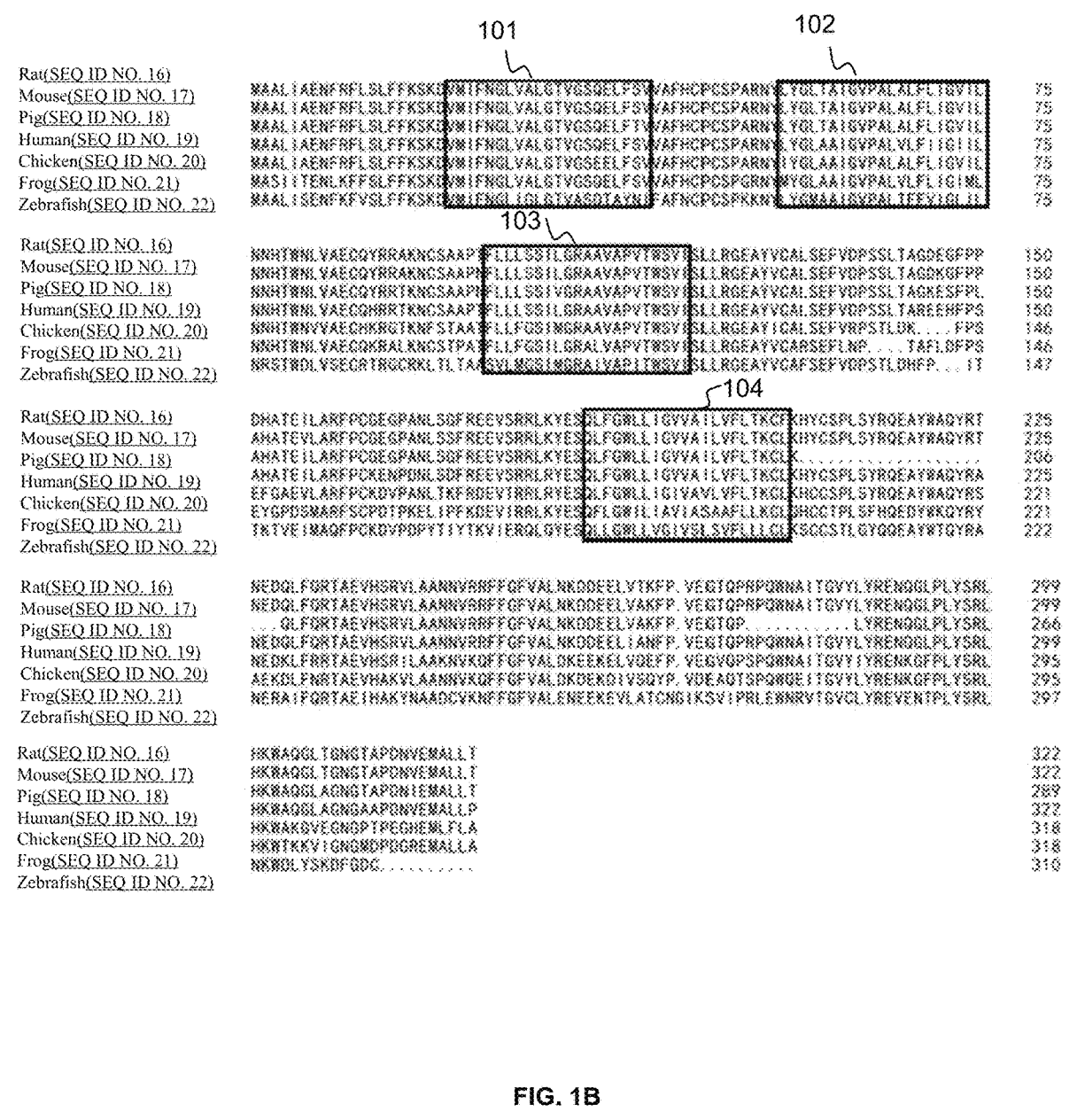

FIG. 1B is an analytical graph of an exemplary comparison of the amino acid sequences of the CALHM2 proteins of some species, as used in some embodiments of the present disclosure. The amino acid sequences of CALHM2 in the rat (SEQ ID NO. 16), the mouse (SEQ ID NO. 17), the pig (SEQ ID NO. 18), the human (SEQ ID NO. 19), the chicken (SEQ ID NO. 20), the frog (SEQ ID NO. 21), and the zebrafish (SEQ ID NO. 22) were compared. The sequence identity among the amino acid sequences of CALHM2 in these species was about 39.692%.

Figure 1C:
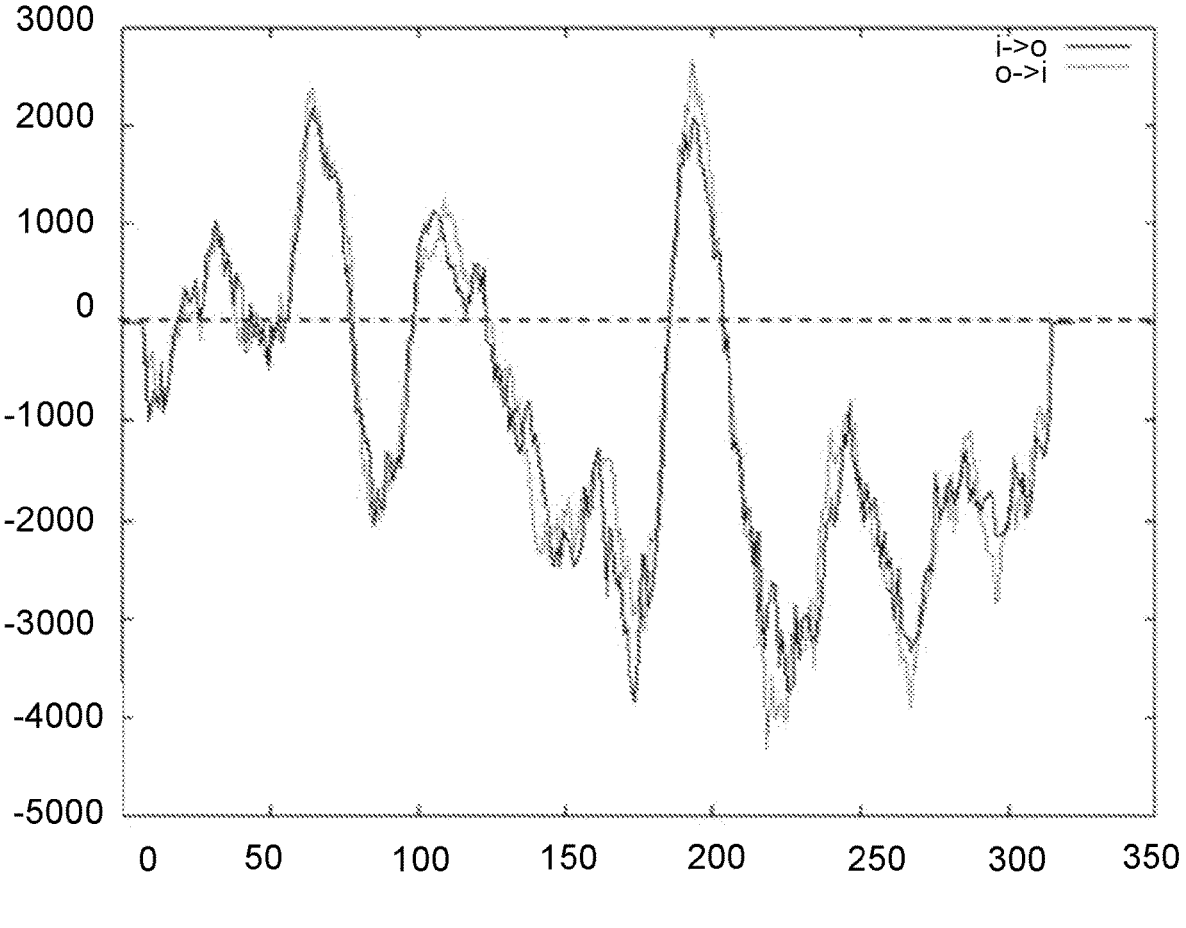
FIG. 1C is an analytical graph illustrating an exemplary prediction result of transmembrane domains of CALHM2 according to some embodiments of the present disclosure.

FIG. 1C is an analytical graph illustrating an exemplary prediction result of transmembrane domains of CALHM2 according to some embodiments of the present disclosure. The prediction was performed using a TMpred program. Similar to CALHM1, CALHM2 was predicted to have four transmembrane domains. The predicted transmembrane domains were marked by the frames 101, 102, 103 and 104 in FIG. 1B.

Example 2 the Expression of CALHM2 in Various Tissues

FIG. 2A is an analytical graph illustrating an exemplary expression of CALHM2 in various organs and tissues according to some embodiments of the present disclosure. The expression of CALHM2 was analyzed using the Tissue-specific Gene Expression and Regulation (TIGER) website. The result suggests that CALHM2 is expressed in many organs and tissue.

As shown in FIG. 2A, no expressed sequence tag of CALHM2 was found in the tongue, the thymus, the small intestine, the lymph node, etc. FIG. 2B is a graph illustrating results of an exemplary western blot analysis for evaluating the expression of CALHM2 in various organs and tissues of mice according to some embodiments of the present disclosure. The CALHM2 was expressed in many important organs such as the brain, the heart, the liver, the spleen, the lung, etc. It was found that the level of expression of CALHM2 was relatively high in some organs, such as the brain, the heart, the kidney, and the liver.

Figure 3A:
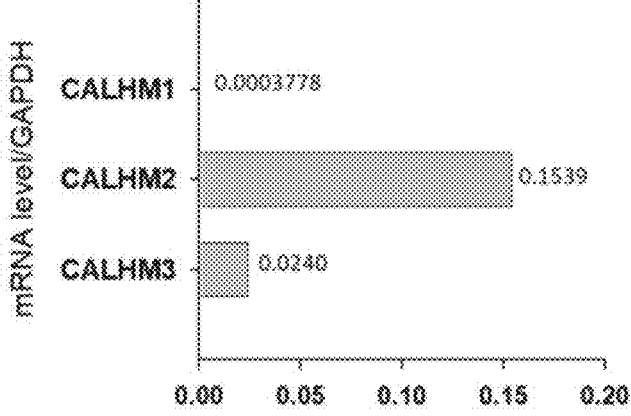
FIG. 3A is an analytical graph illustrating exemplary relative mRNA levels of Calhm1, CALHM2, and Calhm3 in the hearts of the mice according to some embodiments of the present disclosure.
Figure 3B:
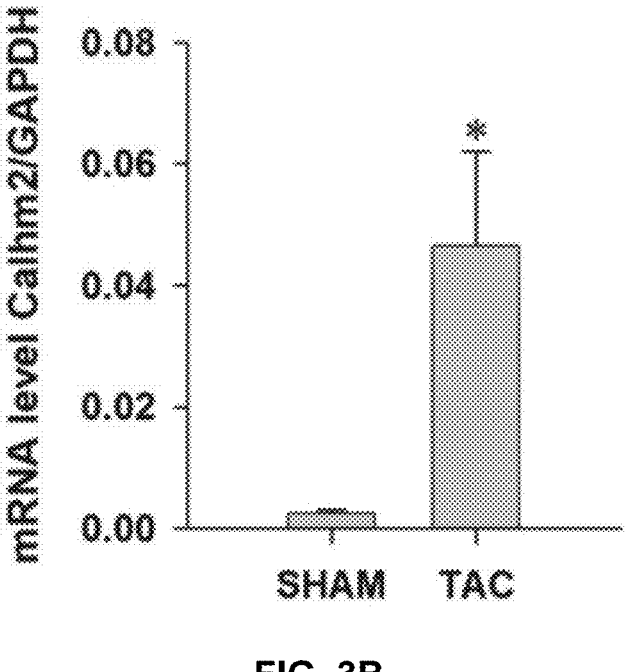
FIG. 3B is an analytical graph illustrating exemplary relative mRNA levels of the hearts of transverse aortic constriction (TAC) mice and SHAM mice according to some embodiments of the present disclosure.

FIG. 3A is an analytical graph illustrating exemplary relative mRNA levels of Calhm1, CALHM2, and Calhm3 in the hearts of the mice according to some embodiments of the present disclosure. The mRNA level of CALHM2 was significantly higher than the mRNA level of CALHM1 and CALHM3. FIG. 3B is an analytical graph illustrating exemplary relative mRNA levels of the hearts of transverse aortic constriction (TAC) mice and SHAM mice according to some embodiments of the present disclosure. For the TAC mice, cardiac hypertrophy and heart failure were introduced by pressure overloading. For the SHAM mice, a sham surgery (placebo surgery) was performed on the mice. The mRNA level in TAC mice was higher than the mRNA level of SHAM mice. These results suggest that CALHM2 may have important functions associated with the heart, such as regulating the functions of the heart.

Example 3 Proteins Having Interactions with CALHM2

CALHM2 polymers were extracted using SDS-PAGE. The CALHM2 polymers were subjected to a denaturing gel electrophoresis. A plurality of proteins were isolated from the CALHM2 polymers and analyzed using mass spectrometry. Some of the identified proteins were shown in Table 2.

TABLE 2

| Exemplary proteins having interactions with CALHM2 | |
|---|---|
| Name of the protein | Description |
| HSP71 | Heat shock 70 kDa protein 1A/1B |
| ATPB | ATP synthase subunit beta, mitochondrial |
| CASPE | Caspase-14 |
| GRP75 | Stress-70 protein, mitochondrial |
| CATA | Catalase |
| NDUS1 | NADH-ubiquinone oxidoreductase 75 kDa subunit, mitochondrial |
| ATD3A | ATPase family AAA domain-constraining protein 3A |
| ATPA | ATP synthase subunit alpha, mitochondrial |
| CLYBL | Citrate lyase subunit beta-like protein, mitochondrial |
| LETM1 | LETM1 and EF-hand domain-containing protein 1, mitochondrial |
| ADCY9 | Adenylate cyclase type 9 |
| ADT1 | ADP/ATP translocase 1 |
| GSHR | Glutahione reductase, mitochondrial |

As shown in Table 2, proteins associated with the electron transport chain of respiration, such as the NDUS1, ADCY9, GSHR, have interactions with CALHM2. Additionally, the heat shock protein (HSP71) and the ATP synthetase have interactions with CALHM2. These results indicate that many proteins located in the mitochondria have interactions with CALHM2. Thus, the CALHM2 may have specific functions related to metabolism in the mitochondria.

Example 4 Knocking Down CALHM2 Affects the Morphology of Mitochondria

Figure 4A:
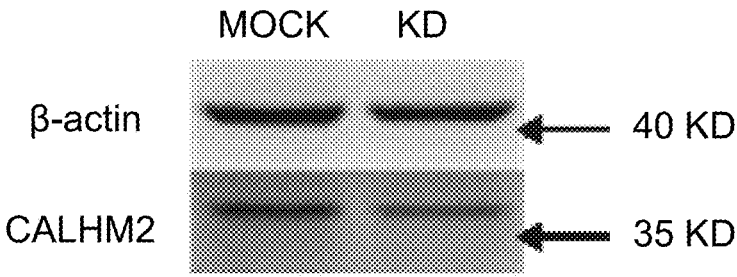
FIG. 4A is a graph illustrating exemplary western blot analysis results associated with the CALHM2 knocked-out (KD) cells and the MOCK cells according to some embodiments of the present disclosure.
Figure 4B:
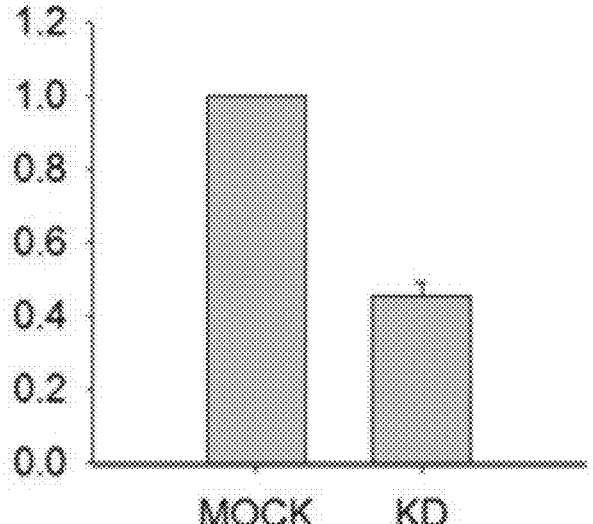
FIG. 4B is an analytical graph illustrating the statistical results of the amount of CALHM2 proteins isolated from the KD cells and the MOCK cells according to some embodiments of the present disclosure.

The CALHM2 gene in COS-7 cells were knocked down using a CRISPR-Cas9 system. The MOCK cells were used as a control group for evaluating various effects of knocking down CALHM2 in COS-7 cells. The expression levels of CALHM2 in the KD cells and the MOCK cells were evaluated by performing a western blot analysis on protein factions isolated from the KD cells and the MOCK cells. FIG. 4A is a graph illustrating exemplary western blot analysis results associated with the CALHM2 knocked-out (KD) cells and the MOCK cells according to some embodiments of the present disclosure. As indicated in FIG. 4A, the expression level of CALHM2 in the KD cells was significantly lower than the expression level of CALHM2 in the MOCK cells. FIG. 4B is an analytical graph illustrating the statistical results of the amount of CALHM2 proteins isolated from the KD cells and the MOCK cells according to some embodiments of the present disclosure. As illustrated in FIG. 4B, the efficiency of knocking down CALHM2 was approximately 60%.

Figure 5A:
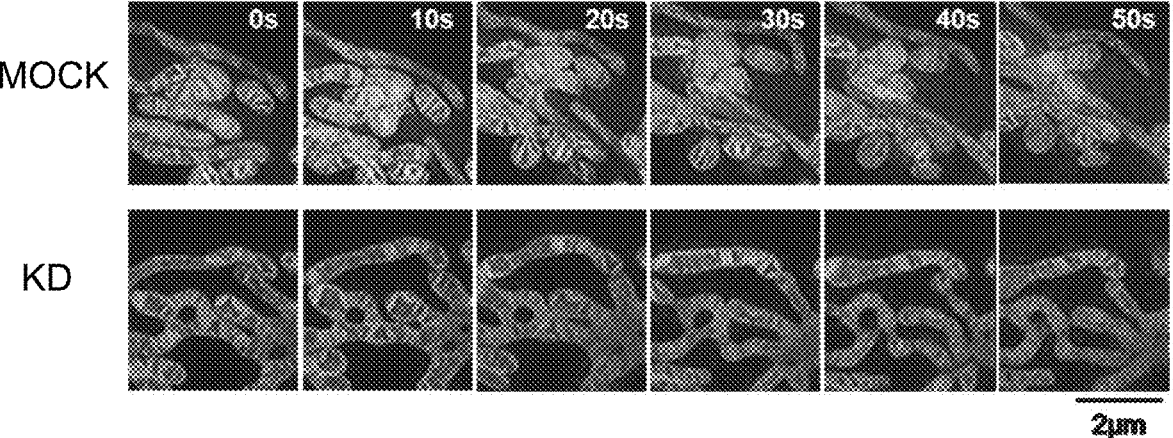
FIG. 5A is a group of photographs of the morphology of the mitochondria in a living MOCK cell and a living KD cell in 50 seconds according to some embodiments of the present disclosure.

The effect of knocking down CALHM2 on the morphology of mitochondria was evaluated. Photographs of the morphology of mitochondria of the MOCK cells and the KD cells were taken every 2 seconds for tracking the dynamic changes of the morphology of the mitochondria of the MOCK cells and the KD cells. FIG. 5A is a group of photographs of the morphology of the mitochondria in a living MOCK cell and a living KD cell in 50 seconds according to some embodiments of the present disclosure. A fission process and a fusion process were observed for the mitochondria of the living cell from the MOCK group.

Figure 5B:
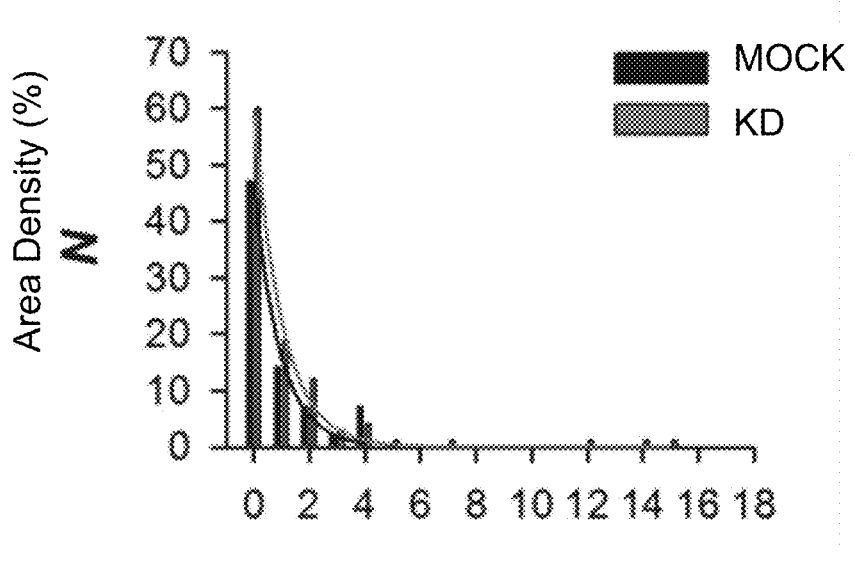
FIG. 5B is an analytical graph illustrating exemplary results of the volume distribution of the mitochondria of the MOCK cells and the KD cells according to some embodiments of the present disclosure.

For the living cell from the KD group, the morphology of the mitochondria was also changed with time, but no fission process or fusion process was observed. Additionally, a reticulum structure of the mitochondria tended to be formed more often in the living cell from the KD group. A globular structure and a strip structure of the mitochondria was observed in the living cell from the MOCK group, but theses mitochondria tended to be stacked upon each other. FIG. 5B is an analytical graph illustrating exemplary results of the volume distribution of the mitochondria of the MOCK cells and the KD cells according to some embodiments of the present disclosure. As illustrated in FIG. 5B, the volume of the mitochondria of the KD cells was generally higher than the volume of the mitochondria of the MOCK cells. Furthermore, the number of the mitochondria having a relatively large volume in the KD cells was greater than that of the MOCK cells.

Figure 5C:
FIGS. 5C and 5D are exemplary electron microscope photographs of the mitochondria of the MOCK cells and the KD cells, respectively, according to some embodiments of the present disclosure.
Figure 5D:
Figure 5E:
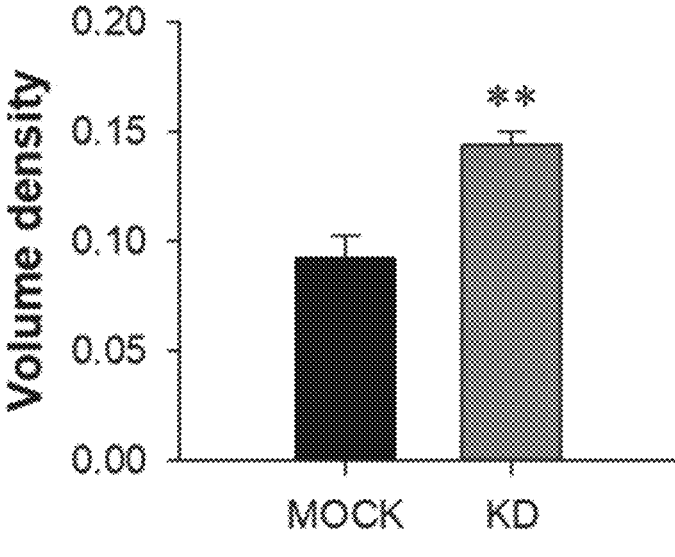
FIG. 5E is an analytical graph illustrating exemplary volume densities of the cristae in the mitochondria of the KD cells and the MOCK cells according to some embodiments of the present disclosure.

The microstructure of the mitochondria of the MOCK cells and the KD cells was observed using the electron microscope. FIGS. 5C and 5D are exemplary electron microscope photographs of the mitochondria of the MOCK cells and the KD cells, respectively, according to some embodiments of the present disclosure. The distribution of the cristae in the mitochondria of the KD cells was observed to be different from the distribution of cristae in the mitochondria of the MOCK cells. As illustrated in FIGS. 5C and 5D, there were more cristae in a mitochondrion of the KD cells than that of the MOCK cells. Some mitochondria of the KD cells were observed to have a shape similar to a tree branch. The cristae junction distance in the mitochondria of the KD cells was less than that of the MOCK cells. This result indicates that the fission process and the fusion process of the mitochondria may be affected after CALHM2 was knocked down. FIG. 5E is an analytical graph illustrating exemplary volume densities of the cristae in the mitochondria of the KD cells and the MOCK cells according to some embodiments of the present disclosure. The volume density (e.g., the density of distribution) of the cristae in the mitochondria of the KD cells was significantly greater than that of the MOCK cells.

Figure 6A:
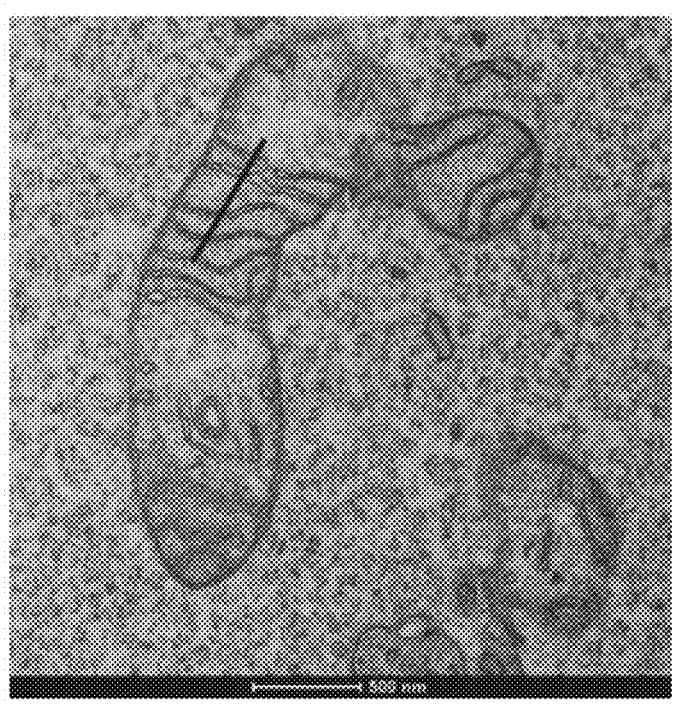
FIGS. 6A and 6B are exemplary electron microscope photographs of the mitochondria of a MOCK cell and a KD cell, respectively with a marking line according to some embodiments of the present disclosure.
Figure 6B:
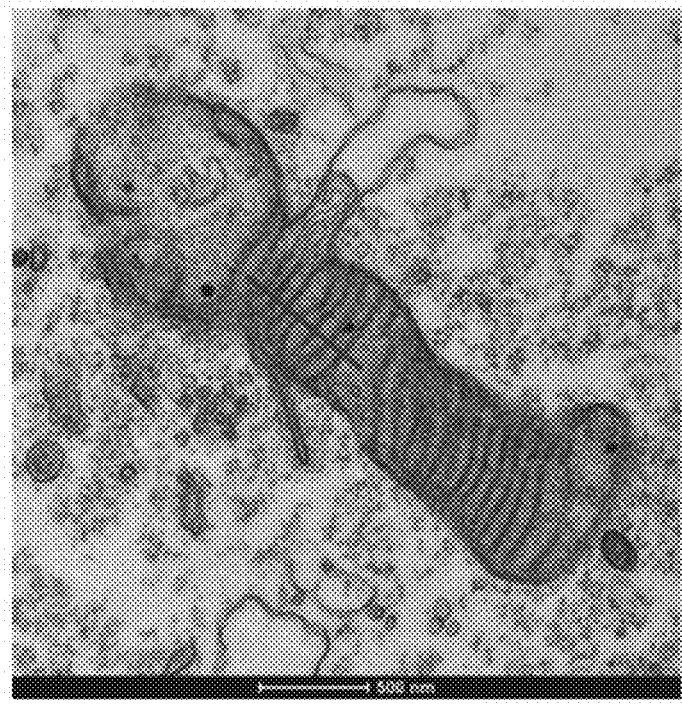
Figure 6C:
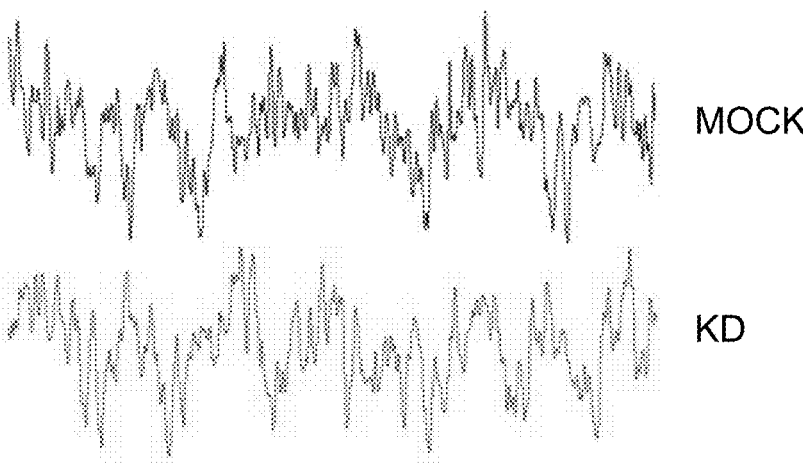
FIG. 6C is an analytical graph illustrating pixel values of pixels along the marking lines in the electron microscope photographs in FIGS. 6A and 6B according to some embodiments of the present disclosure.
Figure 6D:
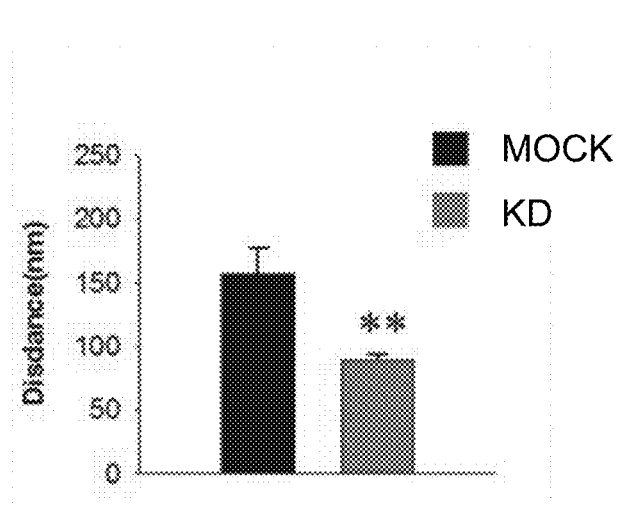
FIG. 6D is an analytical graph illustrating statistic results of exemplary average cristae junction distances for the mitochondria in the MOCK cells and the KD cells according to some embodiments of the present disclosure.

An analysis on the cristae junction distance was further conducted on the MOCK cells and the KD cells. FIGS. 6A and 6B are exemplary electron microscope photographs of the mitochondria of a MOCK cell and a KD cell, respectively with a marking line according to some embodiments of the present disclosure. The length of the marking lines in FIGS. 6A and 6B were equal, and the marking lines were generally perpendicular to the cristae. Pixel values of pixels on the electron microscope photographs along the marking lines were analyzed. FIG. 6C is an analytical graph illustrating pixel values of pixels along the marking lines in the electron microscope photographs in FIGS. 6A and 6B according to some embodiments of the present disclosure. FIG. 6D is an analytical graph illustrating statistic results of exemplary average cristae junction distances for the mitochondria in the MOCK cells and the KD cells according to some embodiments of the present disclosure. The average cristae junction distance for the mitochondria in the KD cells (approximately 89 nm) was significantly less than the average cristae junction distance for the mitochondria in the MOCK cells (approximately 156 nm).

Example 5 Knocking Down CALHM2 Affects the Metabolism of Mitochondria

Figure 7A:
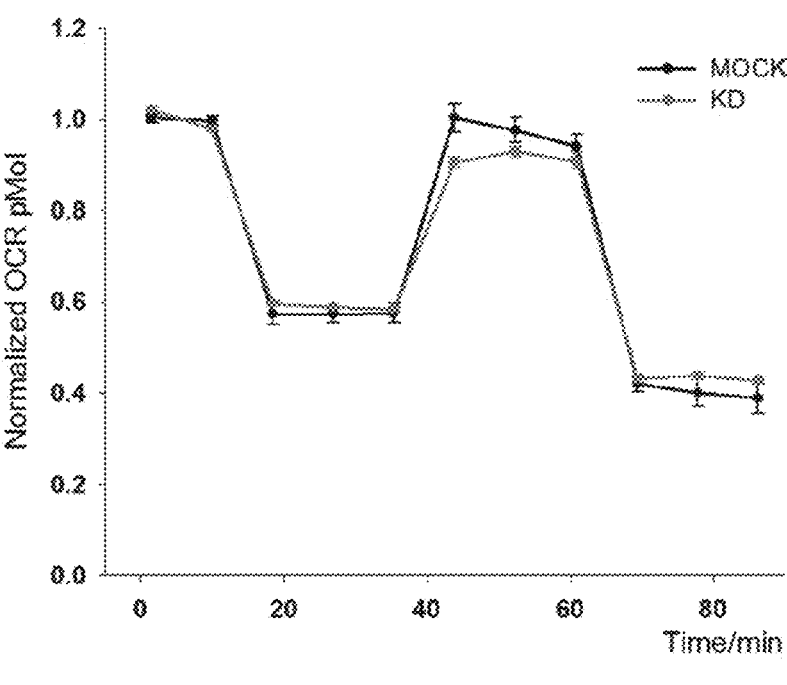
FIG. 7A is an analytical graph illustrating exemplary results of oxygen consumption rate (OCR) of mitochondria in the MOCK cells and the KD cells according to some embodiments of the present disclosure.
Figure 7B:
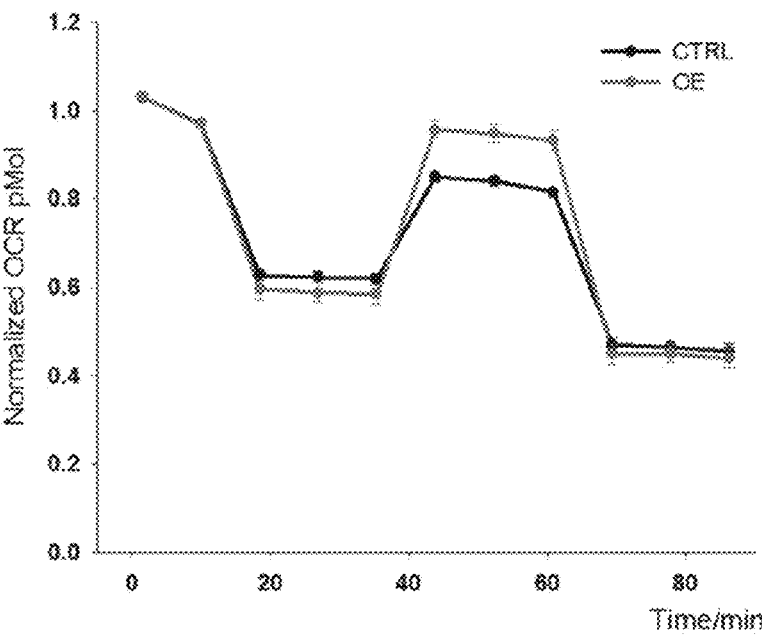
FIG. 7B is an analytical graph illustrating an exemplary evaluation result of OCR of mitochondria in control (CTRL) cells, and CALHM2 over-expressing (OE) cells according to some embodiments of the present disclosure.

FIG. 7A is an analytical graph illustrating exemplary results of oxygen consumption rate (OCR) of mitochondria in the MOCK cells and the KD cells according to some embodiments of the present disclosure. The maximum normalized OCR of the mitochondria in the KD cells was lower than that of the MOCK cells. FIG. 7B is an analytical graph illustrating an exemplary evaluation result of OCR of mitochondria in control (CTRL) cells, and CALHM2 over-expressing (OE) cells according to some embodiments of the present disclosure. The maximum normalized OCR of the mitochondria in the CTRL cells was lower than that of the OE cells. There results indicate that CALHM2 proteins have an effect on the metabolism of mitochondria, for example, on the respiration of the mitochondria.

Example 6 Knocking Out CALHM2 Affects the Size of the Heart

Figure 8A:
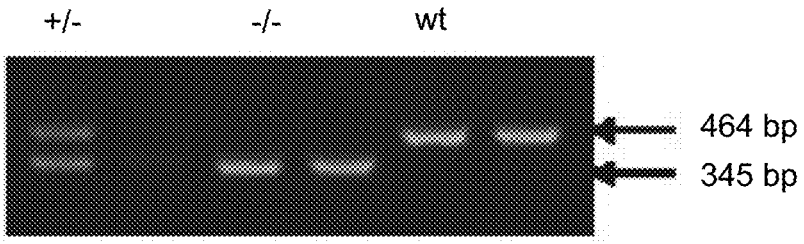
FIG. 8A is an analytical graph illustrating exemplary results of the genotype identification test on the WT mice and KO mice according to some embodiments of the present disclosure.
Figure 8B:
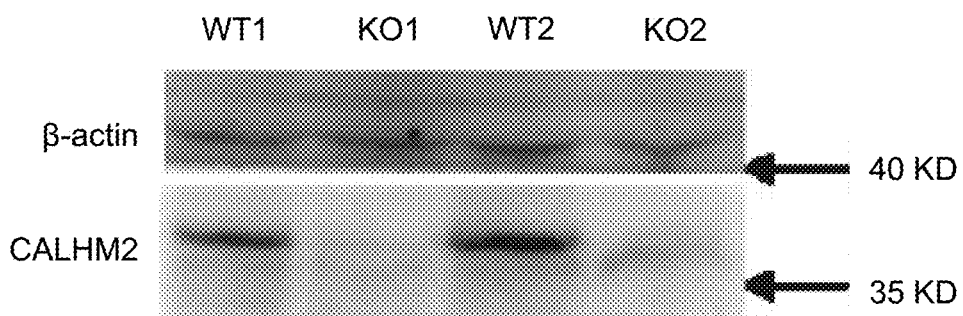
FIG. 8B is an analytical graph illustrating exemplary results of a western blot analysis on the WT mice and the KO mice according to some embodiments of the present disclosure.

The homologous recombination technique was used to knock out CALHM2 in C57BL/6N mice. A genotype identification test was carried out to distinguish wild type (WT) mice and CALHM2 knocked-out (KO) mice. FIG. 8A is an analytical graph illustrating exemplary results of the genotype identification test on the WT mice and KO mice according to some embodiments of the present disclosure. The genotype identification result for the WT mice only included a band of 464 bp, without a band of 345 bp. The genotype identification result for the KO mice only included a band of 345 bp, without a band of 464 bp. FIG. 8B is an analytical graph illustrating exemplary results of a western blot analysis on the WT mice and the KO mice according to some embodiments of the present disclosure. This result demonstrates that CALHM2 proteins are not expressed in the KO mice.

Figure 8C:
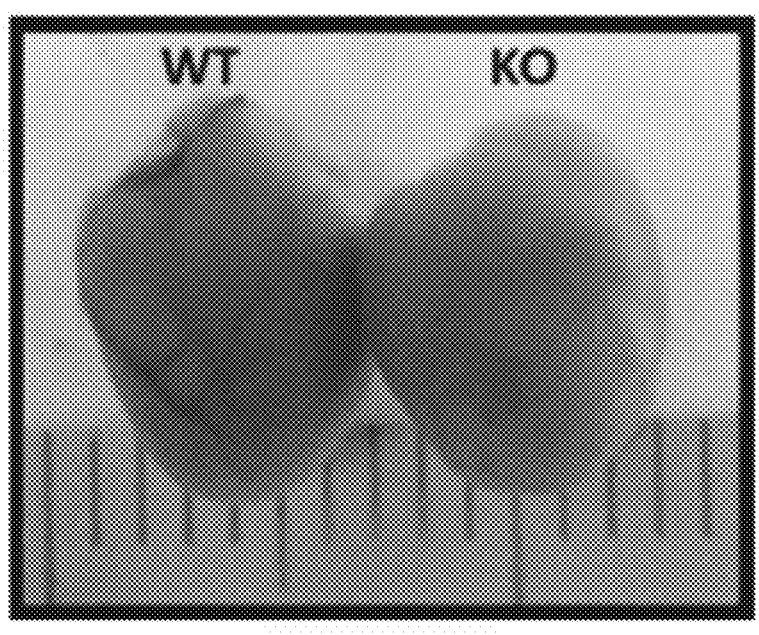
FIG. 8C is an exemplary photograph of the hearts of a pair of WT mouse and KO mouse according to some embodiments of the present disclosure.
Figure 8D:
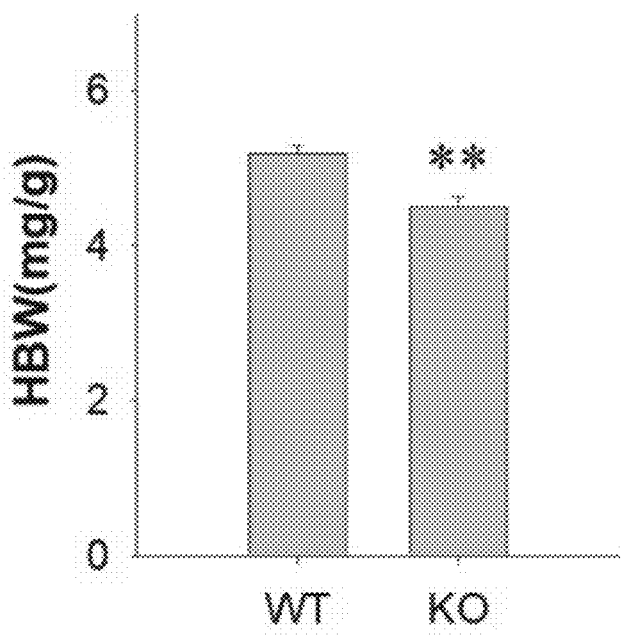
FIG. 8D is an analytical graph illustrating exemplary average ratios of the heart weight to the body weight (HBW) of the WT mice and the KO mice according to some embodiments of the present disclosure.

Five pair of male WT mice and male KO mice (littermates of the male WT mice) at the age of ten weeks were selected for evaluating various effects of knocking out CALHM2 on the mice. No significant difference was observed in the appearance of the WT mice and the KO mice. Surgeries were performed on the WT mice and the KO mice to take out their hearts. FIG. 8C is an exemplary photograph of the hearts of a pair of WT mouse and KO mouse according to some embodiments of the present disclosure. The heart of the KO mouse had a larger size than the heart of the KO mouse. A test was further performed on the weight of the hearts of the WT mice and the KO mice. FIG. 8D is an analytical graph illustrating exemplary average ratios of the heart weight to the body weight (HBW) of the WT mice and the KO mice according to some embodiments of the present disclosure. The average HBW ratio of the KO mice was lower than the average HBW ratio of the WT mice.

Figure 9A:
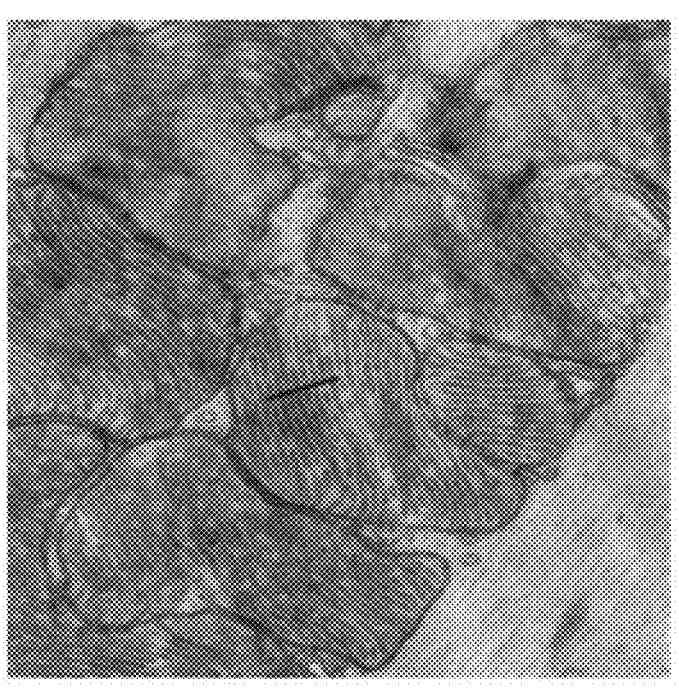
FIGS. 9A and 9B are photographs of an exemplary microstructure of the mitochondria in the cardiomyocytes of a WT mouse and a KO mouse, respectively with a marking line, according to some embodiments of the present disclosure.
Figure 9B:
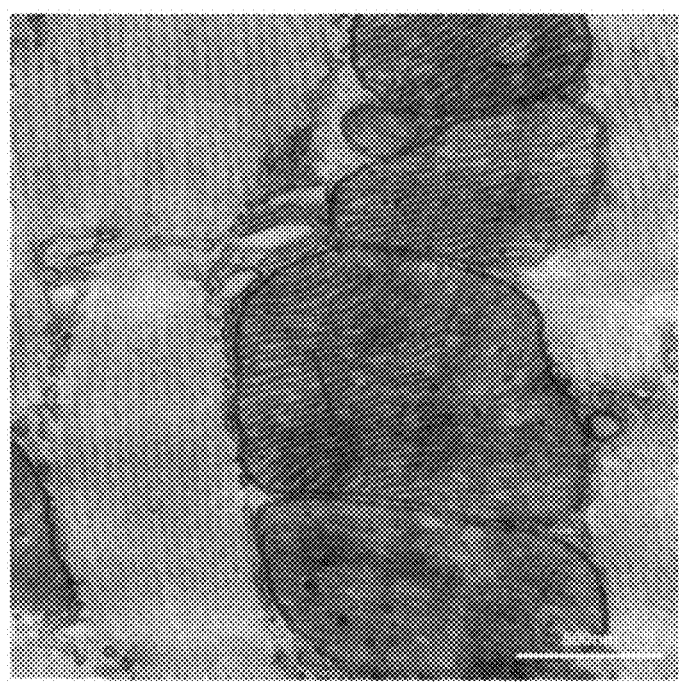
Figure 9C:
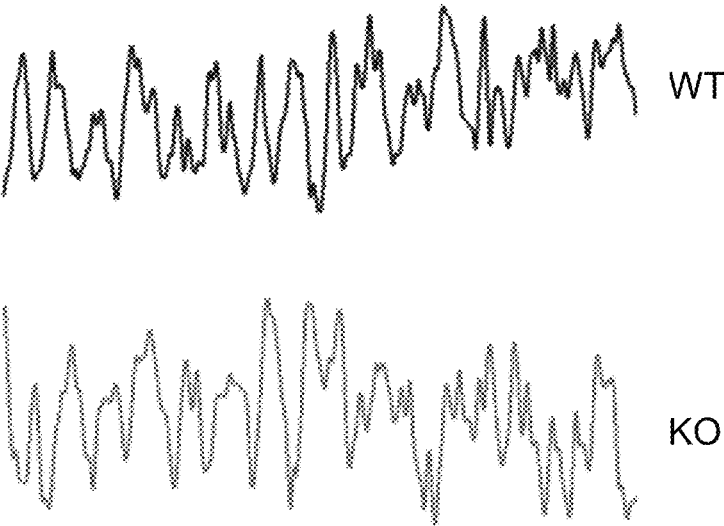
FIG. 9C is an analytical graph illustrating pixel values of pixels along the marking lines in the electron microscope photographs in FIGS. 9A and 9B according to some embodiments of the present disclosure.
Figure 9D:
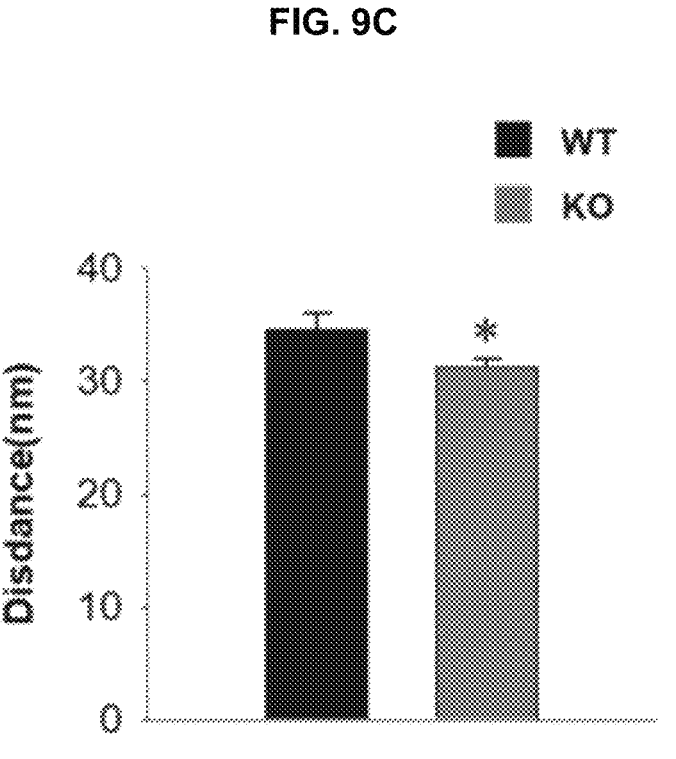
FIG. 9D is an analytical graph illustrating exemplary statistic results of average cristae junction distances for the mitochondria in the cardiomyocytes of the WT mice and the KO mice according to some embodiments of the present disclosure.

Example 7 Knocking Out CALHM2 Affects the Structure and the Metabolism of Mitochondria as Well as the Metabolism of Cardiomyocytes The cardiomyocytes of the WT mice were isolated. The microstructure of the mitochondria in the cardiomyocytes of the WT mice and the KO mice was observed using an electron microscope. FIGS. 9A and 9B are photographs of an exemplary microstructure of the mitochondria in the cardiomyocytes of a WT mouse and a KO mouse, respectively with a marking line, according to some embodiments of the present disclosure. It was observed that the density of distribution of the cristae for the KO mouse was higher than the density of distribution of the cristae for the WT mouse. The length of the marking lines in FIGS. 9A and 9B were equal. Pixel values of pixels on the electron microscope photographs along the marking lines were analyzed. FIG. 9C is an analytical graph illustrating pixel values of pixels along the marking lines in the electron microscope photographs in FIGS. 9A and 9B according to some embodiments of the present disclosure. FIG. 9D is an analytical graph illustrating exemplary statistic results of average cristae junction distances for the mitochondria in the cardiomyocytes of the WT mice and the KO mice according to some embodiments of the present disclosure. Four pairs of WT mice and KO mice were used for determining the average cristae junction distances. For each of the mice, the cristae junction distances of three cardiomyocytes were determined. The average cristae junction distance for the mitochondria in the cardiomyocytes of the KO mice was less than the average cristae junction distance for the mitochondria in the cardiomyocytes of the WT mice.

Figure 10A:
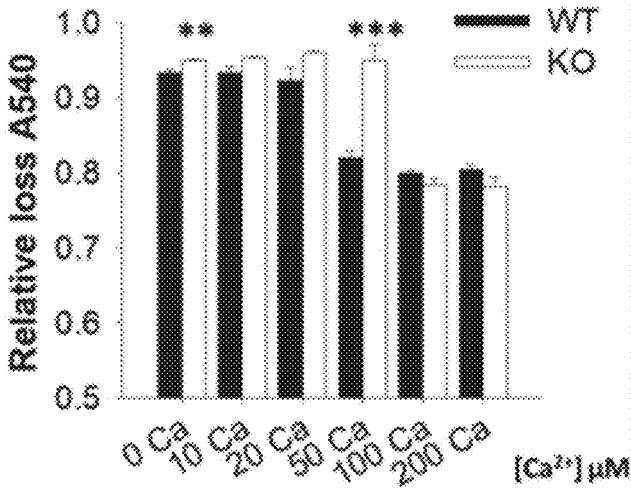
FIG. 10A is an analytical graph illustrating exemplary results of a mitochondrial swelling assay conducted on the mitochondria extracted from the hearts of the WT mice and the KO mice according to some embodiments of the present disclosure.

FIG. 10A is an analytical graph illustrating exemplary results of a mitochondrial swelling assay conducted on the mitochondria extracted from the hearts of the WT mice and the KO mice according to some embodiments of the present disclosure. When the concentration of $CaCl_2$ solution was lower than 50 UM, the mitochondria of the KO mice had less sensitivity to the $Ca^{2+}$ stimuli of than the mitochondria of the WT mice. When the concentration of $CaCl_2$ solution was higher than 50 μM (e.g., 100 μM, 200 μM), no significant difference was found between the sensitivity to the $Ca^{2+}$ stimuli of the mitochondria of the KO mice and that of the WT mice.

Figure 10B:
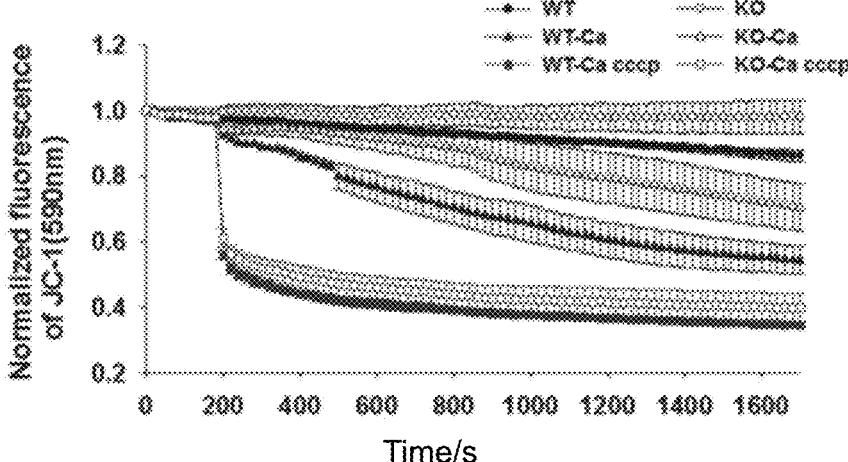
FIG. 10B is an analytical graph illustrating exemplary mitochondrial membrane potential of the KO mice and the WT mice after the $Ca^{2+}$ stimuli according to some embodiments of the present disclosure.

FIG. 10B is an analytical graph illustrating exemplary mitochondrial membrane potential of the KO mice and the WT mice after the $Ca^{2+}$ stimuli according to some embodiments of the present disclosure. It was found that after the $Ca^{2+}$ stimuli at the concentration of 50 μM, the decreasing speed of the mitochondrial membrane potential of the KO mice was lower than that of the WT mice. These results indicate that the mitochondria have more resistance to the $Ca^{2+}$ stimuli within a certain range of concentration when CALHM2 proteins are not expressed in the mitochondria.

Figure 10C:
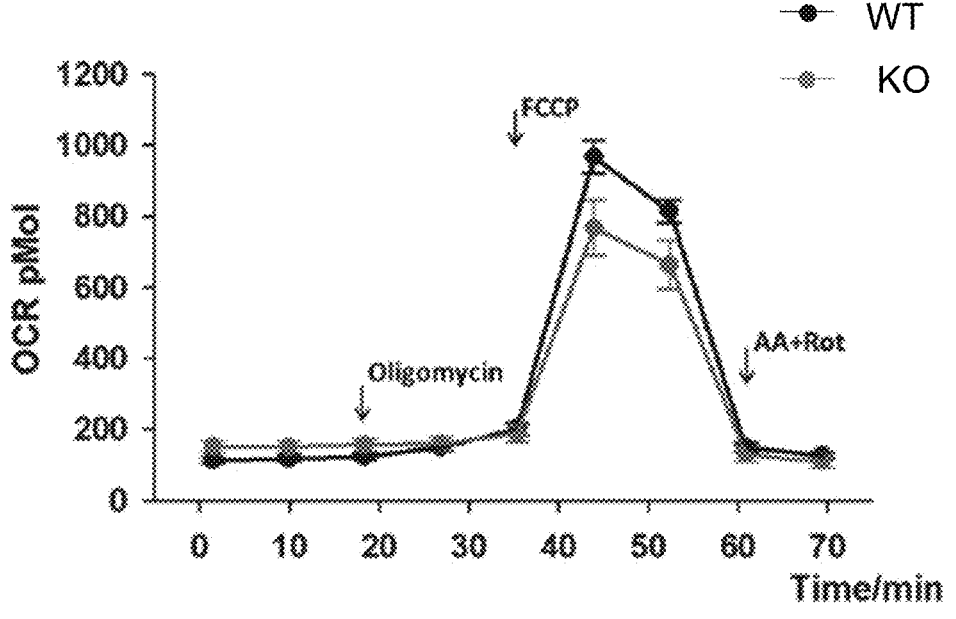
FIG. 10C is an analytical graph illustrating exemplary results of the OCR of the cardiomyocytes of a WT mouse and a KO mouse according to some embodiments of the present disclosure.
Figure 10D:
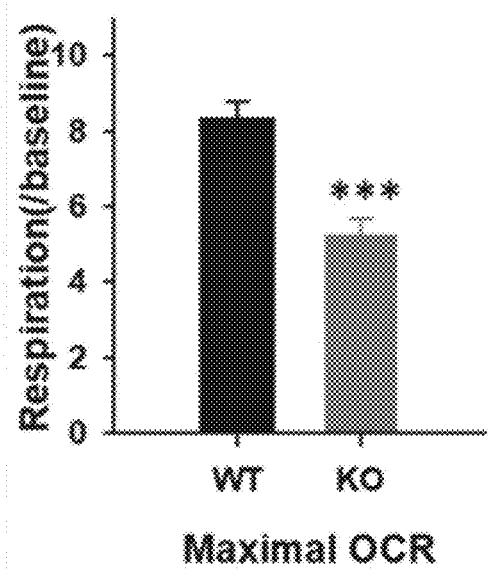
FIG. 10D is an analytical graph illustrating exemplary statistical results of maximum OCRs of the cardiomyocytes of the WT mice and the KO mice according to some embodiments of the present disclosure.
Figure 10E:
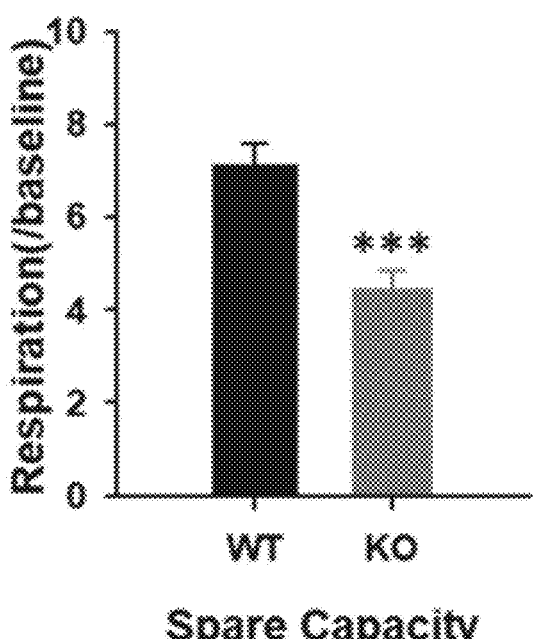
FIG. 10E is an analytical graph illustrating exemplary spare capacities of the cardiomyocytes of the WT mice and the KO mice according to some embodiments of the present disclosure.

FIG. 10C is an analytical graph illustrating exemplary results of the OCR of the cardiomyocytes of a WT mouse and a KO mouse according to some embodiments of the present disclosure. The metabolic efficiency of the cardiomyocytes of the KO mouse was lower than that of the WT mouse. FIG. 10D is an analytical graph illustrating exemplary statistical results of maximum OCRs of the cardiomyocytes of the WT mice and the KO mice according to some embodiments of the present disclosure. The maximum OCR of the cardiomyocytes of the KO mice was lower than that of the WT mouse by 36.4%. FIG. 10E is an analytical graph illustrating exemplary spare capacities of the cardiomyocytes of the WT mice and the KO mice according to some embodiments of the present disclosure. The spare capacity of the KO mice was lower than that of the WT mice by 37.1%. These results indicate that the lack of CALHM2 proteins affects the respiration of the cardiomyocytes.

Example 8 Cardiomyocytes with CALHM2 Deficiency have a Lower Level of Reactive Oxygen Species (ROS)

Figure 11A:
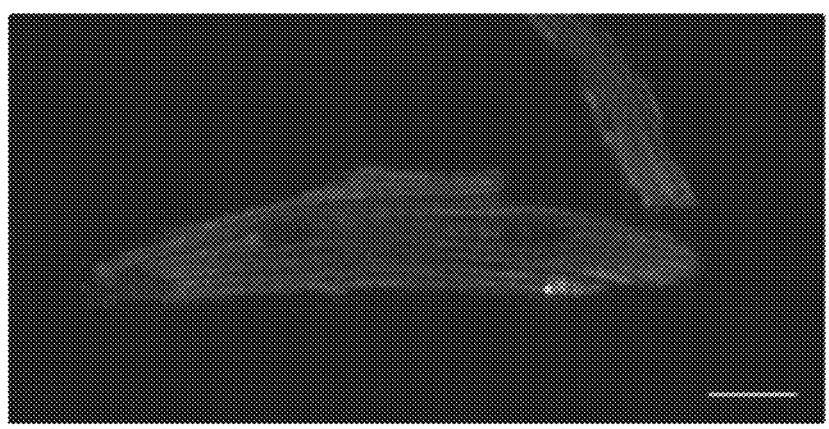
FIG. 11A is a florescent photograph of exemplary cardiomyocytes of the KO mice stained using MitoSox according to some embodiments of the present disclosure.
Figure 11B:
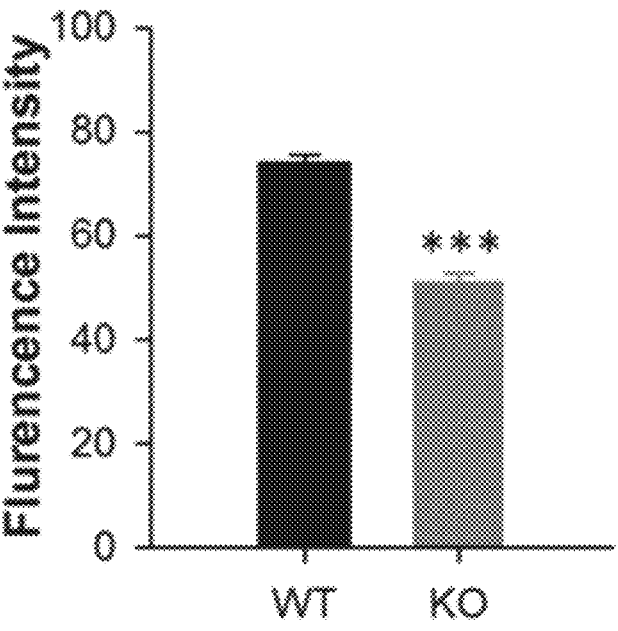
FIG. 11B is an analytical diagram illustrating exemplary average intensities of fluorescence in florescent photographs of the cardiomyocytes of the WT mice and the KO mice according to some embodiments of the present disclosure.

FIG. 11A is a florescent photograph of exemplary cardiomyocytes of the KO mice stained using MitoSox according to some embodiments of the present disclosure. The length of the scaling bar in FIG. 6-6A was 20 μm. The intensity of fluorescence in the florescent photograph was used to evaluate the amount of ROS in the cardiomyocytes. FIG. 11B is an analytical diagram illustrating exemplary average intensities of fluorescence in florescent photographs of the cardiomyocytes of the WT mice and the KO mice according to some embodiments of the present disclosure. As shown in FIG. 11B, the average intensity of florescence corresponding to the KO mice was lower than that of the WT mice. This indicates that cardiomyocytes lacking CALHM2 proteins have lower basal ROS than normal cardiomyocytes. Additionally, this result was in accordance with the resistance of the mitochondria to $Ca^{2+}$ stimuli.

Figure 12A:
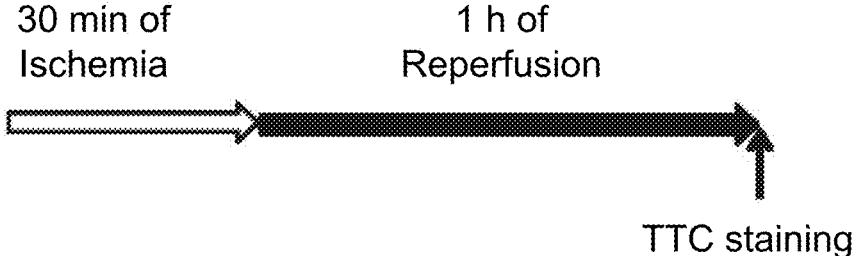
FIG. 12A is a schematic diagram illustrating results of an exemplary ischemia-reperfusion test according to some embodiments of the present disclosure.
Figure 12B:
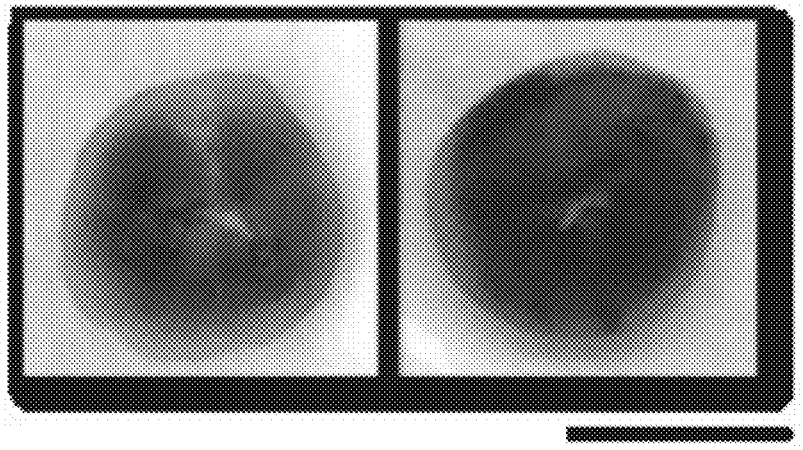
FIG. 12B is a group of photographs of exemplary hearts of the WT mice and the KO mice after the ischemia-reperfusion test according to some embodiments of the present disclosure.
Figure 12C:
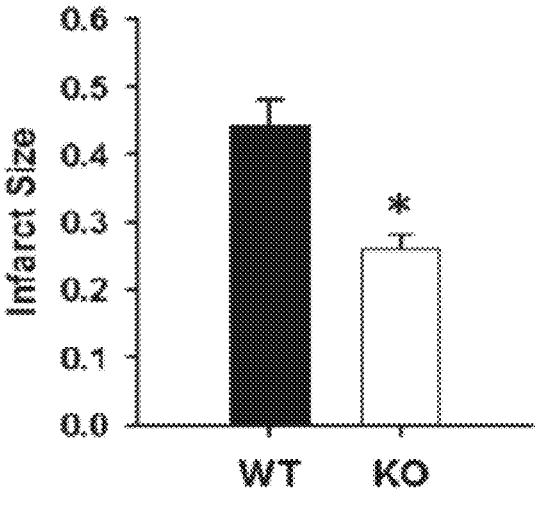
FIG. 12C is an analytical diagram illustrating exemplary average infarct sizes of the hearts of the WT mice and the KO mice after the ischemia-reperfusion test according to some embodiments of the present disclosure.

Example 9 the Heart with CALHM2 Deficiency Showed Less Ischemia-Reperfusion Injury The hearts of the WT mice and the KO mice were removed from their bodies and subjected to an ischemia-reperfusion test. FIG. 12B is a group of photographs of exemplary hearts of the WT mice and the KO mice after the ischemia-reperfusion test according to some embodiments of the present disclosure. The length of the scaling bar in FIG. 12B represents 0.5 cm. As illustrated, the heart of the KO mice (on the right side in FIG. 12B) had less ischemia-reperfusion injury than the heart of the WT mice (on the left side in FIG. 12B). FIG. 12C is an analytical diagram illustrating exemplary average infarct sizes of the hearts of the WT mice and the KO mice after the ischemia-reperfusion test according to some embodiments of the present disclosure. The average infarct size of the KO mice was lower than the average infarct size of the WT mice. These results indicate that the heart where CALHM2 function level is reduced has a certain degree of resistance to metabolic cascades caused by ischemia and reperfusion.

It should be noted that the examples described above are merely provided for the purposes of illustration, and not intended to limit the scope of the present disclosure. For persons having ordinary skill in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

---

We claim:

1. A method of reducing ischemia-reperfusion injury in a subject, comprising:
    administering, to the subject, a pharmaceutical composition including one or more agents that decrease calcium homeostasis modulator 2 (CALHM2) function level in at least one body part of the subject's circulatory system, wherein the at least one body part is the heart of the subject and the one or more agents bind CALHM2 mRNA and are selected from components of a CRISPR-Cas9 system, an aptamer, an antibody, and an siRNA.

2. The method of claim 1, wherein the subject is suffering from cardiac ischemia.

3. The method of claim 1, wherein the one or more agents are configured to decrease CALHM2 function level by reducing CALHM2 protein expression in the at least one body part.

4. The method of claim 1, wherein the one or more agents include aptamers that down-regulate CALHM2 expression.

5. The method of claim 1, wherein the one or more agents include an antibody or a siRNA.

6. A method of reducing reactive oxygen species (ROS) in at least one body part of a subject suffering from a ROS-related disease or condition, comprising:
    administering, to the subject, a pharmaceutical composition including an effective amount of one or more agents that decrease calcium homeostasis modulator 2 (CALHM2) function level in the at least one body part of the subject, wherein the at least one body part of the subject is the heart of the subject, the one or more agents are components of a CRISPR-Cas9 system, and the CALHM2 is decreased with the CRISPR-Cas9 system.

7. The method of claim 6, wherein the one or more agents comprise small molecule guide RNAs (sgRNAs).

8. The method of claim 7, wherein primers encoding the sgRNAs have sequences set forth in SEQ ID NO: 4 and SEQ ID NO: 5.

9. The method of claim 6, wherein the CALHM2 is expressed in mitochondria.

10. The method of claim 6, wherein the subject is a human.

* * * * *

SEQUENCE LISTING

```
<160> NUMBER OF SEQ ID NOS: 22

<210> SEQ ID NO 1
<211> LENGTH: 22
<212> TYPE: DNA
<213> ORGANISM: Artificial Sequence
<220> FEATURE:
<223> OTHER INFORMATION: PCR primer

<400> SEQUENCE: 1
tcctggtgtt cctgaccaag tg                                               22

<210> SEQ ID NO 2
<211> LENGTH: 24
<212> TYPE: DNA
<213> ORGANISM: Artificial Sequence
<220> FEATURE:
<223> OTHER INFORMATION: PCR primer

<400> SEQUENCE: 2
aagtcacctg atgctgaaat gagc                                             24

<210> SEQ ID NO 3
<211> LENGTH: 23
<212> TYPE: DNA
<213> ORGANISM: Artificial Sequence
<220> FEATURE:
<223> OTHER INFORMATION: PCR primer

<400> SEQUENCE: 3
gcatcgcatt gtctgagtag gtg                                              23

<210> SEQ ID NO 4
<211> LENGTH: 23
<212> TYPE: DNA
<213> ORGANISM: artificial sequence
<220> FEATURE:
<223> OTHER INFORMATION: Forward primer sequence for encoding the sgRNA

<400> SEQUENCE: 4
caccgtccgg ccccgaggag gcc                                              23

<210> SEQ ID NO 5
<211> LENGTH: 24
<212> TYPE: DNA
<213> ORGANISM: artificial sequence
<220> FEATURE:
<223> OTHER INFORMATION: Reverse primer sequence for encoding the sgRNA

<400> SEQUENCE: 5
aaactggcct cctcggggcc ggac                                             24

<210> SEQ ID NO 6
<211> LENGTH: 20
<212> TYPE: DNA
<213> ORGANISM: Artificial Sequence
```

-continued

```
<220> FEATURE:
<223> OTHER INFORMATION: PCR primer

<400> SEQUENCE: 6
tcacctggtc tgtcatctcc                                              20

<210> SEQ ID NO 7
<211> LENGTH: 19
<212> TYPE: DNA
<213> ORGANISM: Artificial Sequence
<220> FEATURE:
<223> OTHER INFORMATION: PCR primer

<400> SEQUENCE: 7
tgagtggcga gcagtaatg                                               19

<210> SEQ ID NO 8
<211> LENGTH: 20
<212> TYPE: DNA
<213> ORGANISM: Artificial Sequence
<220> FEATURE:
<223> OTHER INFORMATION: PCR primer

<400> SEQUENCE: 8
tgagtttgtg gacccctcct                                              20

<210> SEQ ID NO 9
<211> LENGTH: 20
<212> TYPE: DNA
<213> ORGANISM: Artificial Sequence
<220> FEATURE:
<223> OTHER INFORMATION: PCR primer

<400> SEQUENCE: 9
gctgagcggt gagcagtaat                                              20

<210> SEQ ID NO 10
<211> LENGTH: 20
<212> TYPE: DNA
<213> ORGANISM: Artificial Sequence
<220> FEATURE:
<223> OTHER INFORMATION: PCR primer

<400> SEQUENCE: 10
gctatttgcg ctgcatctct                                              20

<210> SEQ ID NO 11
<211> LENGTH: 20
<212> TYPE: DNA
<213> ORGANISM: Artificial Sequence
<220> FEATURE:
<223> OTHER INFORMATION: PCR primer

<400> SEQUENCE: 11
ttgagaaagg caacctgcgt                                              20

<210> SEQ ID NO 12
<211> LENGTH: 21
<212> TYPE: DNA
<213> ORGANISM: Artificial Sequence
<220> FEATURE:
<223> OTHER INFORMATION: PCR primer

<400> SEQUENCE: 12
ctgcaaggaa gatgagctgg t                                            21
```

<210> SEQ ID NO 13
<211> LENGTH: 20
<212> TYPE: DNA
<213> ORGANISM: Artificial Sequence
<220> FEATURE:
<223> OTHER INFORMATION: PCR primer

<400> SEQUENCE: 13
tcagacagcg ggctaggaag                                                              20

<210> SEQ ID NO 14
<211> LENGTH: 20
<212> TYPE: DNA
<213> ORGANISM: Artificial Sequence
<220> FEATURE:
<223> OTHER INFORMATION: PCR primer

<400> SEQUENCE: 14
atcaagaagg tggtgaagca                                                              20

<210> SEQ ID NO 15
<211> LENGTH: 21
<212> TYPE: DNA
<213> ORGANISM: Artificial Sequence
<220> FEATURE:
<223> OTHER INFORMATION: PCR primer

<400> SEQUENCE: 15
aaggtggaag aatgggagtt g                                                            21

<210> SEQ ID NO 16
<211> LENGTH: 322
<212> TYPE: PRT
<213> ORGANISM: rat

<400> SEQUENCE: 16

Met Ala Ala Leu Ile Ala Glu Asn Phe Arg Phe Leu Ser Leu Phe Phe
1               5                   10                  15

Lys Ser Lys Asp Val Met Ile Phe Asn Gly Leu Val Ala Leu Gly Thr
                20                  25                  30

Val Gly Ser Gln Glu Leu Phe Ser Val Val Ala Phe His Cys Pro Cys
            35                  40                  45

Ser Pro Ala Arg Asn Tyr Leu Tyr Gly Leu Thr Ala Ile Gly Val Pro
        50                  55                  60

Ala Leu Ala Leu Phe Leu Ile Gly Val Ile Leu Asn Asn His Thr Trp
65                  70                  75                  80

Asn Leu Val Ala Glu Cys Gln Tyr Arg Arg Ala Lys Asn Cys Ser Ala
                85                  90                  95

Ala Pro Thr Phe Leu Leu Leu Ser Ser Ile Leu Gly Arg Ala Ala Val
            100                 105                 110

Ala Pro Val Thr Trp Ser Val Ile Ser Leu Leu Arg Gly Glu Ala Tyr
        115                 120                 125

Val Cys Ala Leu Ser Glu Phe Val Asp Pro Ser Ser Leu Thr Ala Gly
        130                 135                 140

Asp Glu Gly Phe Pro Pro Asp His Ala Thr Glu Ile Leu Ala Arg Phe
145                 150                 155                 160

Pro Cys Gly Glu Gly Pro Ala Asn Leu Ser Gly Phe Arg Glu Glu Val
            165                 170                 175

Ser Arg Arg Leu Lys Tyr Glu Ser Gln Leu Phe Gly Trp Leu Leu Ile
            180                 185                 190

-continued

```
Gly Val Val Ala Ile Leu Val Phe Leu Thr Lys Cys Phe Lys His Tyr
        195                 200                 205

Cys Ser Pro Leu Ser Tyr Arg Gln Glu Ala Tyr Trp Ala Gln Tyr Arg
        210                 215                 220

Thr Asn Glu Asp Gln Leu Phe Gln Arg Thr Ala Glu Val His Ser Arg
225                 230                 235                 240

Val Leu Ala Ala Asn Asn Val Arg Arg Phe Phe Gly Phe Val Ala Leu
                245                 250                 255

Asn Lys Asp Asp Glu Glu Leu Val Thr Lys Phe Pro Val Glu Gly Thr
                260                 265                 270

Gln Pro Arg Pro Gln Trp Asn Ala Ile Thr Gly Val Tyr Leu Tyr Arg
                275                 280                 285

Glu Asn Gln Gly Leu Pro Leu Tyr Ser Arg Leu His Lys Trp Ala Gln
        290                 295                 300

Gly Leu Thr Gly Asn Gly Thr Ala Pro Asp Asn Val Glu Met Ala Leu
305                 310                 315                 320

Leu Thr

<210> SEQ ID NO 17
<211> LENGTH: 322
<212> TYPE: PRT
<213> ORGANISM: mouse

<400> SEQUENCE: 17

Met Ala Ala Leu Ile Ala Glu Asn Phe Arg Phe Leu Ser Leu Phe Phe
1               5                   10                  15

Lys Ser Lys Asp Val Met Ile Phe Asn Gly Leu Val Ala Leu Gly Thr
                20                  25                  30

Val Gly Ser Gln Glu Leu Phe Ser Val Val Ala Phe His Cys Pro Cys
        35                  40                  45

Ser Pro Ala Arg Asn Tyr Leu Tyr Gly Leu Thr Ala Ile Gly Val Pro
        50                  55                  60

Ala Leu Ala Leu Phe Leu Ile Gly Val Ile Leu Asn Asn His Thr Trp
65                  70                  75                  80

Asn Leu Val Ala Glu Cys Gln Tyr Arg Arg Ala Lys Asn Cys Ser Ala
                85                  90                  95

Ala Pro Asn Phe Leu Leu Leu Ser Ser Ile Leu Gly Arg Ala Ala Val
                100                 105                 110

Ala Pro Val Thr Trp Ser Val Ile Ser Leu Leu Arg Gly Glu Ala Tyr
        115                 120                 125

Val Cys Ala Leu Ser Glu Phe Val Asp Pro Ser Ser Leu Thr Ala Gly
        130                 135                 140

Asp Lys Gly Phe Pro Pro Ala His Ala Thr Glu Val Leu Ala Arg Phe
145                 150                 155                 160

Pro Cys Gly Glu Gly Pro Ala Asn Leu Ser Ser Phe Arg Glu Glu Val
                165                 170                 175

Ser Arg Arg Leu Lys Tyr Glu Ser Gln Leu Phe Gly Trp Leu Leu Ile
                180                 185                 190

Gly Val Val Ala Ile Leu Val Phe Leu Thr Lys Cys Leu Lys His Tyr
        195                 200                 205

Cys Ser Pro Leu Ser Tyr Arg Gln Glu Ala Tyr Trp Ala Gln Tyr Arg
        210                 215                 220

Thr Asn Glu Asp Gln Leu Phe Gln Arg Thr Ala Glu Val His Ser Arg
225                 230                 235                 240
```

-continued

```
Val Leu Ala Ala Asn Asn Val Arg Arg Phe Phe Gly Phe Val Ala Leu
            245                 250                 255

Asn Lys Asp Asp Glu Glu Leu Val Ala Lys Phe Pro Val Glu Gly Thr
            260                 265                 270

Gln Pro Arg Pro Gln Trp Asn Ala Ile Thr Gly Val Tyr Leu Tyr Arg
            275                 280                 285

Glu Asn Gln Gly Leu Pro Leu Tyr Ser Arg Leu His Lys Trp Ala Gln
            290                 295                 300

Gly Leu Thr Gly Asn Gly Thr Ala Pro Asp Asn Val Glu Met Ala Leu
305                 310                 315                 320

Leu Thr

<210> SEQ ID NO 18
<211> LENGTH: 289
<212> TYPE: PRT
<213> ORGANISM: pig

<400> SEQUENCE: 18

Met Ala Ala Leu Ile Ala Glu Asn Phe Arg Phe Leu Ser Leu Phe Phe
1               5                   10                  15

Lys Ser Lys Asp Val Met Ile Phe Asn Gly Leu Val Ala Leu Gly Thr
            20                  25                  30

Val Gly Ser Gln Glu Leu Phe Thr Val Val Ala Phe His Cys Pro Cys
            35                  40                  45

Ser Pro Ala Arg Asn Tyr Leu Tyr Gly Leu Thr Ala Ile Gly Val Pro
            50                  55                  60

Ala Leu Ala Leu Phe Leu Ile Gly Val Ile Leu Asn Asn His Thr Trp
65                  70                  75                  80

Asn Leu Val Ala Glu Cys Gln Tyr Arg Arg Thr Lys Asn Cys Ser Ala
            85                  90                  95

Ala Pro Asn Phe Leu Leu Leu Ser Ser Ile Val Gly Arg Ala Ala Val
            100                 105                 110

Ala Pro Val Thr Trp Ser Val Ile Ser Leu Leu Arg Gly Glu Ala Tyr
            115                 120                 125

Val Cys Ala Leu Ser Glu Phe Val Asp Pro Ser Ser Leu Thr Ala Gly
            130                 135                 140

Lys Glu Ser Phe Pro Leu Ala His Ala Thr Glu Ile Leu Ala Arg Phe
145                 150                 155                 160

Pro Cys Gly Glu Gly Pro Ala Asn Leu Ser Gly Phe Arg Glu Glu Val
            165                 170                 175

Ser Arg Arg Leu Lys Tyr Glu Ser Gln Leu Phe Gly Trp Leu Leu Ile
            180                 185                 190

Gly Val Val Ala Ile Leu Val Phe Leu Thr Lys Cys Leu Lys Gln Leu
            195                 200                 205

Phe Gln Arg Thr Ala Glu Val His Ser Arg Val Leu Ala Ala Asn Asn
            210                 215                 220

Val Arg Arg Phe Phe Gly Phe Val Ala Leu Asn Lys Asp Asp Glu Glu
225                 230                 235                 240

Leu Val Ala Lys Phe Pro Val Glu Gly Thr Gln Pro Leu Tyr Arg Glu
            245                 250                 255

Asn Gln Gly Leu Pro Leu Tyr Ser Arg Leu His Lys Trp Ala Gln Gly
            260                 265                 270

Leu Ala Gly Asn Gly Thr Ala Pro Asp Asn Ile Glu Met Ala Leu Leu
            275                 280                 285
```

-continued

Thr

<210> SEQ ID NO 19
<211> LENGTH: 322
<212> TYPE: PRT
<213> ORGANISM: human

<400> SEQUENCE: 19

Met Ala Ala Leu Ile Ala Glu Asn Phe Arg Phe Leu Ser Leu Phe Phe
1               5                   10                  15

Lys Ser Lys Asp Val Met Ile Phe Asn Gly Leu Val Ala Leu Gly Thr
                20                  25                  30

Val Gly Ser Gln Glu Leu Phe Ser Val Val Ala Phe His Cys Pro Cys
            35                  40                  45

Ser Pro Ala Arg Asn Tyr Leu Tyr Gly Leu Ala Ala Ile Gly Val Pro
        50                  55                  60

Ala Leu Val Leu Phe Ile Ile Gly Ile Ile Leu Asn Asn His Thr Trp
65                  70                  75                  80

Asn Leu Val Ala Glu Cys Gln His Arg Arg Thr Lys Asn Cys Ser Ala
                85                  90                  95

Ala Pro Thr Phe Leu Leu Leu Ser Ser Ile Leu Gly Arg Ala Ala Val
            100                 105                 110

Ala Pro Val Thr Trp Ser Val Ile Ser Leu Leu Arg Gly Glu Ala Tyr
            115                 120                 125

Val Cys Ala Leu Ser Glu Phe Val Asp Pro Ser Ser Leu Thr Ala Arg
        130                 135                 140

Glu Glu His Phe Pro Ser Ala His Ala Thr Glu Ile Leu Ala Arg Phe
145                 150                 155                 160

Pro Cys Lys Glu Asn Pro Asp Asn Leu Ser Asp Phe Arg Glu Glu Val
                165                 170                 175

Ser Arg Arg Leu Arg Tyr Glu Ser Gln Leu Phe Gly Trp Leu Leu Ile
            180                 185                 190

Gly Val Val Ala Ile Leu Val Phe Leu Thr Lys Cys Leu Lys His Tyr
            195                 200                 205

Cys Ser Pro Leu Ser Tyr Arg Gln Glu Ala Tyr Trp Ala Gln Tyr Arg
        210                 215                 220

Ala Asn Glu Asp Gln Leu Phe Gln Arg Thr Ala Glu Val His Ser Arg
225                 230                 235                 240

Val Leu Ala Ala Asn Asn Val Arg Arg Phe Phe Gly Phe Val Ala Leu
                245                 250                 255

Asn Lys Asp Asp Glu Glu Leu Ile Ala Asn Phe Pro Val Glu Gly Thr
                260                 265                 270

Gln Pro Arg Pro Gln Trp Asn Ala Ile Thr Gly Val Tyr Leu Val Arg
            275                 280                 285

Glu Asn Gln Gly Leu Pro Leu Tyr Ser Arg Leu His Lys Trp Ala Gln
        290                 295                 300

Gly Leu Ala Gly Asn Gly Ala Ala Pro Asp Asn Tyr Glu Met Ala Leu
305                 310                 315                 320

Leu Pro

<210> SEQ ID NO 20
<211> LENGTH: 318
<212> TYPE: PRT
<213> ORGANISM: chicken

-continued

```
<400> SEQUENCE: 20

Met Ala Ala Leu Ile Ala Glu Asn Phe Arg Phe Leu Ser Leu Phe Phe
1               5                   10                  15

Lys Ser Lys Asp Val Met Ile Phe Asn Gly Leu Val Ala Leu Gly Thr
            20                  25                  30

Val Gly Ser Glu Glu Leu Phe Ser Val Val Ala Phe His Cys Pro Cys
        35                  40                  45

Ser Pro Ala Arg Asn Tyr Ile Tyr Gly Leu Ala Ala Ile Gly Val Pro
    50                  55                  60

Ala Leu Ala Leu Phe Leu Ile Gly Val Ile Leu Asn Asn His Thr Trp
65                  70                  75                  80

Asn Val Val Ala Glu Cys His Lys Arg Gly Thr Lys Asn Phe Ser Thr
                85                  90                  95

Ala Ala Thr Phe Leu Leu Phe Gly Ser Ile Met Gly Arg Ala Ala Val
            100                 105                 110

Ala Pro Val Thr Trp Ser Val Ile Ser Leu Leu Arg Gly Glu Ala Tyr
            115                 120                 125

Ile Cys Ala Leu Ser Glu Phe Val Arg Pro Ser Thr Leu Asp Lys Phe
        130                 135                 140

Pro Ser Glu Phe Gly Ala Glu Val Leu Ala Arg Phe Pro Cys Lys Asp
145                 150                 155                 160

Val Pro Ala Asn Leu Thr Lys Phe Arg Asp Glu Val Thr Arg Arg Leu
                165                 170                 175

Arg Tyr Glu Ser Gln Leu Phe Gly Trp Leu Leu Ile Gly Ile Val Ala
            180                 185                 190

Val Leu Val Phe Leu Thr Lys Cys Leu Lys His Cys Cys Ser Pro Leu
            195                 200                 205

Ser Tyr Arg Gln Glu Ala Tyr Trp Ala Gln Tyr Arg Ser Asn Glu Asp
    210                 215                 220

Lys Leu Phe Arg Arg Thr Ala Glu Val His Ser Arg Ile Leu Ala Ala
225                 230                 235                 240

Lys Asn Val Lys Ala Phe Phe Gly Phe Val Ala Leu Asp Lys Glu Glu
                245                 250                 255

Lys Glu Leu Val Gln Glu Phe Pro Val Glu Gly Val Gln Pro Ser Pro
            260                 265                 270

Gln Trp Asn Ala Ile Thr Gly Val Tyr Ile Tyr Arg Glu Asn Lys Gly
            275                 280                 285

Phe Pro Leu Tyr Ser Arg Leu His Lys Trp Ala Lys Gly Val Glu Gly
    290                 295                 300

Asn Gly Pro Thr Pro Glu Gly His Glu Met Leu Phe Leu Ala
305                 310                 315

<210> SEQ ID NO 21
<211> LENGTH: 318
<212> TYPE: PRT
<213> ORGANISM: frog

<400> SEQUENCE: 21

Met Ala Ser Ile Ile Thr Glu Asn Leu Lys Phe Phe Ser Leu Phe Phe
1               5                   10                  15

Lys Ser Lys Asp Val Met Ile Phe Asn Gly Leu Val Ala Leu Gly Thr
            20                  25                  30

Val Gly Ser Gln Glu Leu Phe Ser Val Val Ala Phe His Cys Pro Cys
        35                  40                  45
```

-continued

```
Ser Pro Gly Arg Asn Tyr Met Tyr Gly Leu Ala Ala Ile Gly Val Pro
    50              55                  60

Ala Leu Val Leu Phe Leu Ile Gly Ile Met Leu Asn Asn His Thr Trp
65              70                  75                  80

Asn Leu Val Ala Glu Cys Gln Lys Arg Ala Leu Lys Asn Cys Ser Thr
                85                  90                  95

Pro Ala Thr Phe Leu Leu Phe Gly Ser Ile Leu Gly Arg Ala Leu Val
                100                 105                 110

Ala Pro Val Thr Trp Ser Val Ile Ser Leu Leu Arg Gly Glu Ala Tyr
                115                 120                 125

Val Cys Ala Arg Ser Glu Phe Leu Asn Pro Thr Ala Phe Leu Asp Phe
    130                 135                 140

Pro Ser Glu Tyr Gly Pro Asp Ser Met Ala Arg Phe Ser Cys Pro Asp
145                 150                 155                 160

Thr Pro Lys Glu Leu Ile Pro Phe Lys Asp Glu Val Ile Arg Arg Leu
                165                 170                 175

Lys Tyr Glu Ser Gln Phe Leu Gly Trp Ile Leu Ile Ala Val Ile Ala
                180                 185                 190

Ser Ala Ala Phe Leu Leu Lys Cys Leu Gln His Cys Cys Thr Pro Leu
                195                 200                 205

Ser Phe His Gln Glu Asp Tyr Trp Lys Gln Tyr Arg Tyr Ala Glu Lys
    210                 215                 220

Asp Leu Phe Asn Arg Thr Ala Glu Val His Ala Lys Val Leu Ala Ala
225                 230                 235                 240

Asn Asn Val Lys Ala Phe Phe Gly Phe Val Ala Leu Asp Lys Asp Glu
                245                 250                 255

Lys Asp Ile Val Ser Gln Tyr Pro Val Asp Glu Ala Gln Thr Ser Pro
                260                 265                 270

Gln Trp Gln Glu Ile Thr Gly Val Tyr Leu Tyr Arg Glu Asn Lys Gly
    275                 280                 285

Phe Pro Leu Tyr Ser Arg Leu His Lys Trp Thr Lys Lys Val Ile Gly
    290                 295                 300

Asn Gly Met Asp Pro Asp Gly Arg Glu Met Ala Leu Leu Ala
305                 310                 315

<210> SEQ ID NO 22
<211> LENGTH: 310
<212> TYPE: PRT
<213> ORGANISM: zebrafish

<400> SEQUENCE: 22

Met Ala Ala Leu Ile Ser Glu Asn Phe Lys Phe Val Ser Leu Phe Phe
1               5                   10                  15

Lys Ser Lys Asp Val Met Ile Phe Asn Gly Leu Ile Gly Leu Gly Thr
                20                  25                  30

Val Ala Ser Gln Thr Ala Tyr Asn Ile Phe Ala Phe Asn Cys Pro Cys
            35                  40                  45

Ser Pro Lys Lys Asn Tyr Leu Tyr Gly Met Ala Ala Ile Gly Val Pro
    50              55                  60

Ala Leu Thr Phe Phe Val Ile Gly Leu Ile Leu Asn Arg Ser Thr Trp
65              70                  75                  80

Asp Leu Val Ser Glu Cys Arg Thr Arg Gly Cys Arg Lys Leu Thr Leu
                85                  90                  95

Thr Ala Ala Ser Val Leu Met Gly Ser Ile Met Gly Arg Ala Ile Val
                100                 105                 110
```

-continued

```
Ala Pro Ile Thr Trp Ser Val Ile Ser Leu Leu Arg Gly Glu Ala Tyr
        115             120                 125

Val Cys Ala Phe Ser Glu Phe Val Asp Pro Ser Thr Leu Asp His Phe
    130             135                 140

Pro Ile Thr Thr Lys Thr Val Glu Ile Met Ala Gln Phe Pro Cys Lys
145             150                 155                 160

Asp Val Pro Asp Pro Tyr Thr Ile Tyr Thr Lys Val Ile Glu Arg Gln
                165                 170                 175

Leu Gln Tyr Glu Ser Gln Leu Leu Gly Trp Leu Leu Val Gly Ile Val
            180             185                 190

Ser Leu Ser Val Phe Leu Leu Leu Cys Leu Lys Ser Cys Cys Ser Thr
        195             200                 205

Leu Gly Tyr Gln Gln Glu Ala Tyr Trp Thr Gln Tyr Arg Ala Asn Glu
    210             215                 220

Arg Ala Ile Phe Gln Arg Thr Ala Glu Ile His Ala Lys Tyr Asn Ala
225             230                 235                 240

Ala Asp Cys Val Lys Asn Phe Phe Gly Phe Val Ala Leu Glu Asn Glu
            245             250                 255

Glu Lys Glu Val Leu Ala Thr Cys Asn Gly Ile Lys Ser Val Ile Pro
            260             265                 270

Arg Leu Glu Trp Asn Arg Val Thr Gly Val Cys Leu Tyr Arg Glu Val
        275             280                 285

Glu Asn Thr Pro Leu Tyr Ser Arg Leu Asn Lys Trp Asp Leu Tyr Ser
    290             295                 300

Lys Asp Phe Gly Asp Cys
305             310
```